(12) United States Patent
Parry et al.

(10) Patent No.: US 8,101,726 B2
(45) Date of Patent: Jan. 24, 2012

(54) LIGANDS BINDING THE COMPLEX OF UROKINASE-TYPE PLASMINOGEN ACTIVATOR (UPA) AND ITS RECEPTOR (UPAR) THAT INHIBIT DOWNSTREAM UPAR INTERACTIONS: IDENTIFICATION AND USE IN DIAGNOSIS OR THERAPY

(75) Inventors: Graham C. Parry, San Mateo, CA (US); Andrew P. Mazar, San Diego, CA (US)

(73) Assignee: Tactic Pharma, LLC, Evanston, IL (US)

( * ) Notice: Subject to any disclaimer, the term of this patent is extended or adjusted under 35 U.S.C. 154(b) by 643 days.

(21) Appl. No.: 11/597,689

(22) PCT Filed: May 25, 2005

(86) PCT No.: PCT/US2005/018322
§ 371 (c)(1),
(2), (4) Date: Sep. 25, 2007

(87) PCT Pub. No.: WO2005/116077
PCT Pub. Date: Dec. 8, 2005

(65) Prior Publication Data
US 2009/0180952 A1    Jul. 16, 2009

Related U.S. Application Data

(60) Provisional application No. 60/573,896, filed on May 25, 2004.

(51) Int. Cl.
*C07K 16/28* (2006.01)
*C07K 16/00* (2006.01)
*A61K 39/395* (2006.01)

(52) U.S. Cl. ............. 530/388.22; 530/388.1; 530/387.1; 424/143.1; 424/141.1

(58) Field of Classification Search .................. None
See application file for complete search history.

(56) References Cited

U.S. PATENT DOCUMENTS

2003/0219837 A1* 11/2003 Cress et al. .................... 435/7.2
2004/0197863 A1* 10/2004 Luther et al. ................. 435/69.1

OTHER PUBLICATIONS

Blasi et al. Nature Reviews: Molecular Cell Biology, 2002, 3:932-943.*
Bauer, T.W. et al., Insulin-like Growth Factor-I—Mediated Migration and Invasion of Human Colon Carcinoma Cells Requires Activation of c-Met and Urokinase Plasminogen Activator Receptor, Annals of Surgery 241:748-758 (May 2005).
Bauer, T.W. et al., Targeting of Urokinase Plasminogen Activator Receptor in Human Pancreatic Carcinoma Cells Inhibits c-Met—and Insulin-like Growth Factor-I Receptor—Mediated Migration and Invasion and Orthotopic Tumor Growth in Mice, Cancer Res. 65:7775-7781 (Sep. 2005).
Van Buren G et al., Targeting the Urokinase Plasminogen Activator Receptor With a Monoclonal Antibody Impairs the Growth of Human Colorectal Cancer in the Liver, Cancer 115:3360-68 (Jul. 2009).
Rabbani, S.A. et al., An Anti—Urokinase Plasminogen Activator Receptor Antibody (ATN-658) Blocks Prostate Cancer Invasion, Migration, Growth, and Experimental Skeletal Metastasis in Vitro and in vivo, Neoplasia 12:778-788 (Oct. 2010).
Kenny, H.A. et al., Targeting the Urokinase Plasminogen Activator Receptor Inhibits Ovarian Cancer Metastasis, Clin. Cancer Res. 17:459-471 (Feb. 2011).
Mosaic Laboratories, LLC, Optimization and Validation of ATN-658 for the Detection of uPAR by Immunohistochemistry: A Validation Study, 2007.
Mazar, Andrew P., Presentation: "Targeting the urokinase plasminogen activator (uPA) system for the treatment of cancer" 2011.

* cited by examiner

*Primary Examiner* — Sharon Wen
(74) *Attorney, Agent, or Firm* — Browdy and Neimark, PLLC

(57) ABSTRACT

Antibodies or other ligands specific for the binary uPA-uPAR complexes, for ternary complexes comprising uPA-uPAR and for complexes of uPAR and proteins other than uPA such as integrins inhibit the interaction of uPA and uPAR with additional molecules with which the complexed interact. Such antibodies or other ligands are used in diagnostic and therapeutic methods, particularly against cancer.

27 Claims, 11 Drawing Sheets

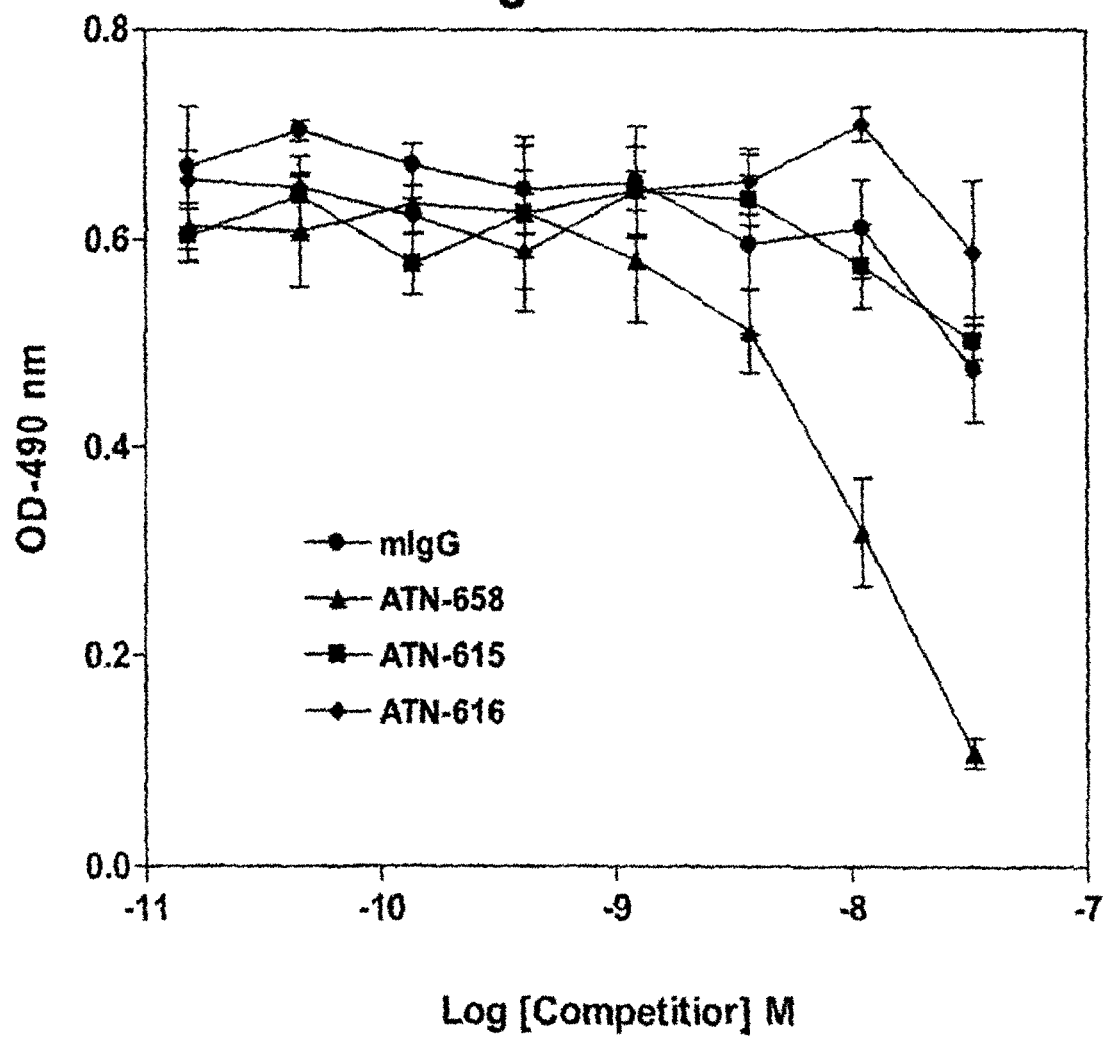

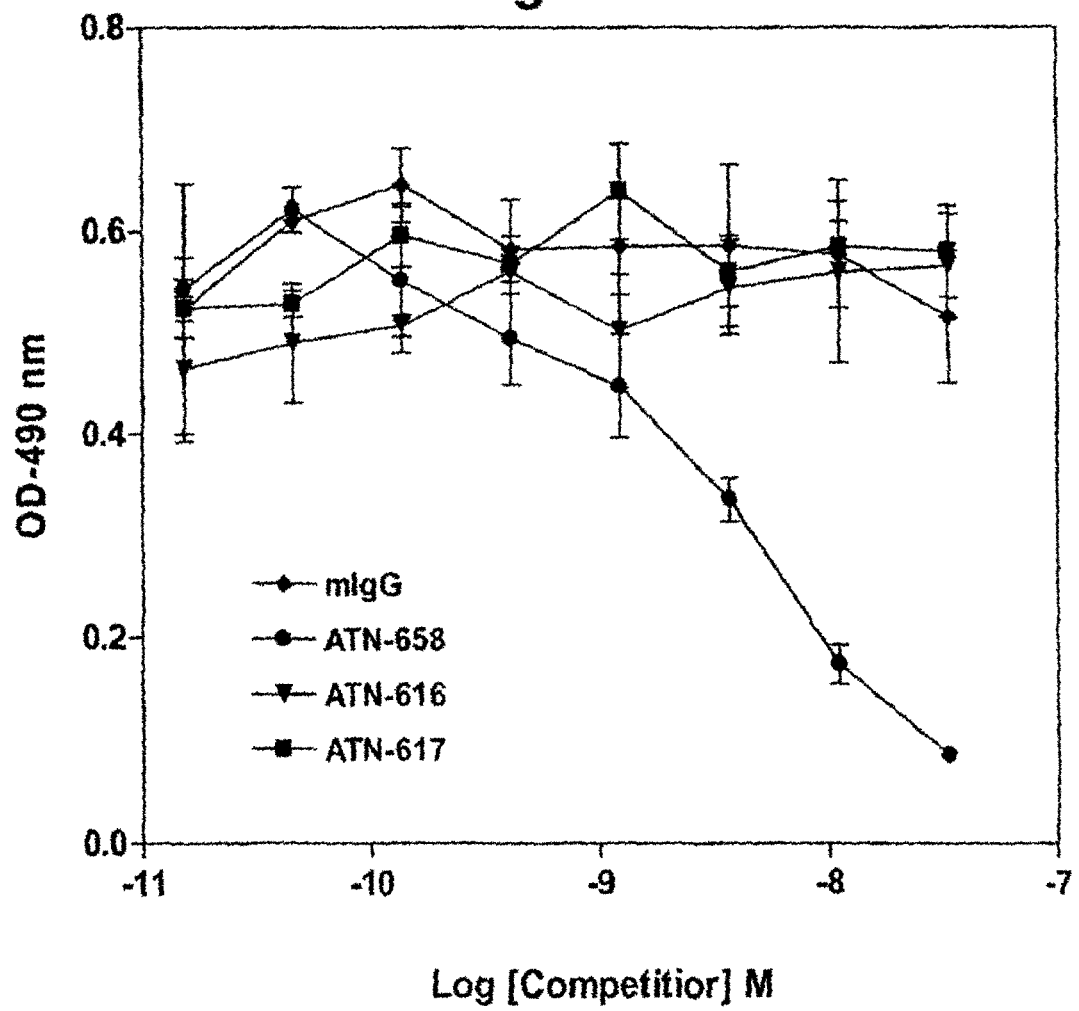

SEQUENCE LISTING

<160> NUMBER OF SEQ ID NOS: 16

<210> SEQ ID NO 1
<211> LENGTH: 113
<212> TYPE: PRT
<213> ORGANISM: Artificial sequence
<220> FEATURE:
<223> OTHER INFORMATION: Consensus sequence of part of immunoglobulin
      chain
<220> FEATURE:
<221> NAME/KEY: MISC_FEATURE
<222> LOCATION: (3)..(3)
<223> OTHER INFORMATION: Xaa can be any amino acid

<400> SEQUENCE: 1

Asp Ile Xaa Leu Thr Gln Ser Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Leu Thr Phe Gly Ala Gly Thr Lys Leu Glu Leu Lys
            100                 105                 110

Leu

<210> SEQ ID NO 2
<211> LENGTH: 117
<212> TYPE: PRT
<213> ORGANISM: Artificial sequence
<220> FEATURE:
<223> OTHER INFORMATION: Consensus sequence of part of immunoglobulin
      chain

<400> SEQUENCE: 2

Val Gln Leu Gln Glu Ser Gly Pro Glu Leu Val Lys Thr Gly Ala Ser
1               5                   10                  15

Val Lys Ile Ser Cys Lys Ala Ser Gly Tyr Ser Phe Thr Ser Tyr Tyr
            20                  25                  30

```
Met His Trp Val Lys Gln Ser His Gly Lys Ser Leu Glu Trp Ile Gly
        35                  40                  45

Glu Ile Asn Pro Tyr Asn Gly Gly Ala Ser Tyr Asn Gln Lys Ile Lys
 50                  55                  60

Gly Arg Ala Thr Phe Thr Val Asp Thr Ser Ser Arg Thr Ala Tyr Met
 65                  70                  75                  80

Gln Phe Asn Ser Leu Thr Ser Glu Asp Ser Ala Val Tyr Tyr Cys Ala
                 85                  90                  95

Arg Ser Ile Tyr Gly His Ser Val Leu Asp Tyr Trp Gly Gln Gly Thr
                100                 105                 110

Thr Val Thr Val Ser
            115

<210> SEQ ID NO 3
<211> LENGTH: 16
<212> TYPE: PRT
<213> ORGANISM: Artificial sequence
<220> FEATURE:
<223> OTHER INFORMATION: Consensus sequence of part of immunoglobulin
      chain

<400> SEQUENCE: 3

Lys Ser Ser Gln Ser Leu Leu Asp Ser Asp Gly Lys Thr Tyr Leu Asn
 1               5                  10                  15

<210> SEQ ID NO 4
<211> LENGTH: 7
<212> TYPE: PRT
<213> ORGANISM: Artificial sequence
<220> FEATURE:
<223> OTHER INFORMATION: Consensus sequence of part of immunoglobulin
      chain

<400> SEQUENCE: 4

Leu Val Ser Lys Leu Asp Ser
 1               5

<210> SEQ ID NO 5
<211> LENGTH: 9
<212> TYPE: PRT
<213> ORGANISM: Artificial sequence
<220> FEATURE:
<223> OTHER INFORMATION: Consensus sequence of part of immunoglobulin
      chain

<400> SEQUENCE: 5

Trp Gln Gly Thr His Phe Pro Leu Thr
 1               5

<210> SEQ ID NO 6
<211> LENGTH: 10
<212> TYPE: PRT
<213> ORGANISM: Artificial sequence
<220> FEATURE:
<223> OTHER INFORMATION: Consensus sequence of part of immunoglobulin
      chain

<400> SEQUENCE: 6

Gly Tyr Ser Phe Thr Ser Tyr Tyr Met His
 1               5                  10

<210> SEQ ID NO 7
<211> LENGTH: 17
<212> TYPE: PRT
<213> ORGANISM: Artificial sequence
```

-continued

```
<220> FEATURE:
<223> OTHER INFORMATION: Consensus sequence of part of immunoglobulin
      chain

<400> SEQUENCE: 7

Glu Ile Asn Pro Tyr Asn Gly Gly Ala Ser Tyr Asn Gln Lys Ile Lys
1               5                   10                  15

Gly

<210> SEQ ID NO 8
<211> LENGTH: 10
<212> TYPE: PRT
<213> ORGANISM: Artificial sequence
<220> FEATURE:
<223> OTHER INFORMATION: Consensus sequence of part of immunoglobulin
      chain

<400> SEQUENCE: 8

Ser Ile Tyr Gly His Ser Val Leu Asp Tyr
1               5                   10

<210> SEQ ID NO 9
<211> LENGTH: 106
<212> TYPE: PRT
<213> ORGANISM: Artificial sequence
<220> FEATURE:
<223> OTHER INFORMATION: Consensus sequence of part of immunoglobulin
      chain

<400> SEQUENCE: 9

Asp Ile Val Leu Thr Gln Ser Pro Asp Ile Thr Ala Ala Ser Leu Gly
1               5                   10                  15

Gln Lys Val Thr Ile Thr Cys Ser Ala Ser Ser Ser Val Ser Tyr Met
            20                  25                  30

His Trp Tyr Gln Gln Lys Ser Gly Thr Ser Pro Lys Pro Trp Ile Phe
        35                  40                  45

Glu Ile Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Ile Tyr Tyr Cys Gln Gln Trp Asn Tyr Pro Phe Thr Phe
                85                  90                  95

Gly Gly Gly Thr Lys Leu Glu Ile Lys Arg
            100                 105

<210> SEQ ID NO 10
<211> LENGTH: 117
<212> TYPE: PRT
<213> ORGANISM: Artificial sequence
<220> FEATURE:
<223> OTHER INFORMATION: Consensus sequence of part of immunoglobulin
      chain

<400> SEQUENCE: 10

Val Lys Leu Gln Gln Ser Gly Pro Glu Val Val Lys Pro Gly Ala Ser
1               5                   10                  15

Val Lys Ile Ser Cys Lys Ala Ser Gly Tyr Ser Phe Thr Asn Phe Tyr
            20                  25                  30

Ile His Trp Val Lys Gln Arg Pro Gly Gln Gly Leu Glu Trp Ile Gly
        35                  40                  45

Trp Ile Phe His Gly Ser Asp Asn Thr Glu Tyr Asn Glu Lys Phe Lys
    50                  55                  60
```

```
Asp Lys Ala Thr Leu Thr Ala Asp Thr Ser Ser Ser Thr Ala Tyr Met
 65                  70                  75                  80

Gln Leu Ser Ser Leu Thr Ser Glu Asp Ser Ala Val Tyr Phe Cys Ala
                 85                  90                  95

Arg Trp Gly Pro His Trp Tyr Phe Asp Val Trp Gly Gln Gly Thr Thr
            100                 105                 110

Val Thr Val Ser Ser
            115

<210> SEQ ID NO 11
<211> LENGTH: 10
<212> TYPE: PRT
<213> ORGANISM: Artificial sequence
<220> FEATURE:
<223> OTHER INFORMATION: Consensus sequence of part of immunoglobulin
      chain

<400> SEQUENCE: 11

Ser Ala Ser Ser Ser Val Ser Tyr Met His
1               5                   10

<210> SEQ ID NO 12
<211> LENGTH: 7
<212> TYPE: PRT
<213> ORGANISM: Artificial sequence
<220> FEATURE:
<223> OTHER INFORMATION: Consensus sequence of part of immunoglobulin
      chain

<400> SEQUENCE: 12

Glu Ile Ser Lys Leu Ala Ser
1               5

<210> SEQ ID NO 13
<211> LENGTH: 8
<212> TYPE: PRT
<213> ORGANISM: Artificial sequence
<220> FEATURE:
<223> OTHER INFORMATION: Consensus sequence of part of immunoglobulin
      chain

<400> SEQUENCE: 13

Gln Gln Trp Asn Tyr Pro Phe Thr
1               5

<210> SEQ ID NO 14
<211> LENGTH: 10
<212> TYPE: PRT
<213> ORGANISM: Artificial sequence
<220> FEATURE:
<223> OTHER INFORMATION: Consensus sequence of part of immunoglobulin
      chain

<400> SEQUENCE: 14

Gly Tyr Ser Phe Thr Asn Phe Tyr Ile His
1               5                   10

<210> SEQ ID NO 15
<211> LENGTH: 17
<212> TYPE: PRT
<213> ORGANISM: Artificial sequence
<220> FEATURE:
<223> OTHER INFORMATION: Consensus sequence of part of immunoglobulin
      chain

<400> SEQUENCE: 15

Trp Ile Phe His Gly Ser Asp Asn Thr Glu Tyr Asn Glu Lys Phe Lys
```

```
1               5                  10                 15
Asp

<210> SEQ ID NO 16
<211> LENGTH: 9
<212> TYPE: PRT
<213> ORGANISM: Artificial sequence
<220> FEATURE:
<223> OTHER INFORMATION: Consensus sequence of part of immunoglobulin
      chain

<400> SEQUENCE: 16

Trp Gly Pro His Trp Tyr Phe Asp Val
1               5
```

LIGANDS BINDING THE COMPLEX OF UROKINASE-TYPE PLASMINOGEN ACTIVATOR (UPA) AND ITS RECEPTOR (UPAR) THAT INHIBIT DOWNSTREAM UPAR INTERACTIONS: IDENTIFICATION AND USE IN DIAGNOSIS OR THERAPY

This application is the U.S. national phase of PCT Application PCT/US2005/018322 filed on May 25, 2005, which claims priority to U.S. provisional application Ser. No. 60/573,896, filed May 25, 2004.

BACKGROUND OF THE INVENTION

1. Field of the Invention

The present invention in the field of biochemistry, immunology and medicine relates to antibodies ("Abs") or other ligands specific for (a) the binary uPA-uPAR complexes, (b) ternary complexes comprising uPA-uPAR and (c) complexes of uPAR and proteins other than uPA such as integrins. These Abs or non-Ab ligands inhibit the interaction of uPA and uPAR with additional molecules with which the above complexes interact. Such Abs or other non-Ab ligands are used in diagnostic and therapeutic methods, particularly against cancer.

2. Description of the Background Art

A significant body of evidence from studies in vitro and in vivo has established that the urokinase plasminogen activator (uPA) system is central to the process of metastasis, making it a promising target for cancer drug development (Mazar, A P et al. (1999) *Angiogenesis* 3: 15-32). In addition to uPA, its cell surface receptor (uPAR) is a suitable target for the design and development of cancer therapeutic and diagnostic agents (Mazar, A P (2001) *Anti-Cancer Drugs* 12: 397-400) because:

(a) uPAR is selectively expressed on metastatic tumor cells and angiogenic endothelial cells ("ECs"), but not on other cells;
(b) uPAR is an important participant in several extracellular and intracellular pathways required for metastasis that are currently the object of intense drug development efforts; and
(c) it is possible to interfere at several different points along the uPA pathway.

Thus, uPA and uPAR are promising targets for the development of diagnostics and therapeutics useful against many different types of tumors/cancers.

The uPA/uPAR System and Cancer

Metastasis and angiogenesis share many common functional features that characterize invasive and migratory processes of tumor cells and of ECs. These features include (1) the up-regulation of protease and integrin expression, (2) the loss of cell-cell and cell-matrix contacts, (3) increased responsiveness to growth and differentiation factors, and (4) remodeling of extracellular matrix (ECM) and basement membrane (BasM). All of these contribute to tumor progression.

The uPA "system," which comprises the serine protease uPA, its receptor uPAR, and its specific serpin inhibitor, plasminogen activator inhibitor-type 1 (PAI-1), plays a central role in many of these activities. The activity of this system is responsible for:

(1) initiating cascades that result in the activation of plasminogen, activating several pro-metalloproteases (proMMPs),
(2) release and processing of latent growth factors such as fibroblast growth factor-2 (FGF-2), vascular endothelial growth factor (VEGF), hepatocyte growth factor (HGF), and transforming growth factor-1 (TGFβ),
(3) (a) interactions with components of the ECM such as vitronectin (Vn) and fibronectin (Fn),
(b) direct interactions with several integrins including α5β1 and αvβ3, and (c) remodeling of the BasM and ECM to promote cell motility.

Further, the uPA system can also initiate localized fibrin turnover which may play a role in angiogenesis.

The expression of uPA and uPAR has been demonstrated in numerous tumor types including glioblastoma, prostate, breast, colon, hepatocellular, and renal cell carcinoma. (Mizukami I F et al. (1994) *Clin Immunol and Immunopathol* 71:96-104; Hsu D W et al., (1995) *Am J Pathol* 147:114-23; de Witte J H et al. (1999) *Br J Cancer* 79:1190-8). The expression of uPA and uPAR are typically greater in more aggressive forms of disease. On tumor cells, this expression is often highest at the invasive front of the tumor. (Buo, L et al., (1995) *Human Pathol* 26:1133-1138; Yamamoto M et al. (1994) *Cancer Res* 54:5016-5020). Strong immunohistochemical staining for uPAR in blood vessels associated with the invasive front of breast, colon, and renal cell carcinomas has been reported (Bastholm L et al. *Appl Immunohistochem Mol Morphol* 7: 39-47; Nakata S et al. (1998) *Int. J. Cancer* 79:179-186). In the colon carcinoma study, uPAR co-localized with VEGF. The expression of uPA and uPAR has also been observed on tumor-associated macrophages in several tumor types (Ohtani H et al. (1995) *Int J Cancer* 62:691-6; Xu Y et al. (1997) *Hum Pathol* 28:206-13). uPA is chemotactic for monocytes and mediates both adhesion and migration of these cells. Adhesion and migration require only uPAR occupancy but not uPA catalytic activity. Thus, the uPA system is believed to contribute to tumor progression by acting on multiple tumor-associated cell types.

Several recent studies have evaluated the therapeutic potential of inhibiting the binding of uPA to uPAR in syngeneic systems. The delivery of an adenovirus-encoded murine amino-terminal fragment of uPA (abbreviated "ATF"—this is the domain of uPA that contains the uPAR binding region) directly into tumors resulted in (a) suppression of neovascularization and (b) arrest of tumor growth (Li H et al. (1998) *Gene Ther* 5:1105-1113). Due to species "specificity," murine ATF would be expected to bind only to murine host ECs and leukocytes, not to human tumor cells. This indicates that the tumor inhibition was mediated through the suppression of the host angiogenic response. Finally, a collaborative study between some of the present inventors and S. Rabbani and J. Gladu recently demonstrated that a polyclonal Ab raised against a 100-residue fragment of rat uPAR selectively localized to a rat breast tumor which grew from cells of the Mat BIII cell line (Rabbani S A et al. (2002) *Cancer Res* 62:2390-97). This polyclonal antibody completely inhibited tumor growth and led to tumor regression.

Unfortunately, despite the promise of targeting the uPA system for therapeutic and diagnostic purposes, research efforts have not resulted in the development of agents suitable for the clinic. Small molecule approaches have been hampered by (1) the difficulty of potently inhibiting a protein-protein interaction (e.g., uPA-uPAR or uPAR-integrin), and (2) the lack of suitable leads or structural information amenable to medicinal chemistry efforts. Several potent peptide inhibitors of the uPA-uPAR interaction have been identified but these would suffer from the typically poor pharmacological properties of peptides and have not demonstrated the requisite levels of activity even in cell-based assays (Ploug M et al. (2001) *Biochemistry* 40:12157-68).

SUMMARY OF THE INVENTION

The present inventors produced a set of monoclonal antibodies (mabs) that bind to uPA-uPAR complexes and that inhibit their interaction of with downstream targets such as integrins. Such inhibition is expected to inhibit tumor growth and metastasis. These mAbs may have utility as "naked" antibodies as well as for targeting therapeutic agents and imaging agents to tumors. Several antibodies that target uPAR are effective in animal models of cancer growth (the A2780 ovarian cancer model and the A549 lung cancer model). The epitopes recognized by these mAbs are peptide regions within uPAR. Therefore uPAR peptides corresponding to these regions or derived therefrom are useful as antagonists of uPAR interactions with downstream proteins.

It is common for malignant tumor cells and angiogenic ECs to gain a selective advantage in the process of cell migration and invasiveness. This advantage results at least in part from the cells' expression of uPAR molecules on their surface, and these uPAR molecules are saturated by binding the endogenously produced ligand, uPA.

Thus, mabs, peptides or other chemical entities that target and preferably inhibit uPA-uPAR interactions with downstream targets are useful in the treatment and/or diagnosis of cancer. Preferred downstream ligands of uPA-uPAR, or of uPAR alone, include integrins, low-density lipoprotein receptor-related protein (LRP) as well as other binding partners. Some of these downstream ligands may mediate cell signaling, migration and/or invasion.

The present inventors have produced and studied two mabs, ATN-615 and ATN-658, that specifically bind ligand-occupied uPAR and thus serve as exemplary molecules that can bind uPAR regardless of the presence of ligand. The mAbs can detect both occupied and unoccupied uPAR in a tumor or other diseased tissue where the uPA system plays a role in the pathobiology. Preferred Abs or other non-Ab ligands are those that do not bind to the uPA-binding site of uPAR.

The present inventors have identified the epitopes to which these Abs bind. Such peptides or natural or synthetic peptides or peptide derivatives that retain the 3D structure of these epitopes are useful as therapeutic and/or diagnostic agents. Several peptide sequences identified based on these epitopes are disclosed herein.

In addition, the present inventors have developed a method to identify Abs that mimic the characteristics of ATN-615 and ATN-658. This method can be used to develop humanized or fully human mAbs that recognize and bind to the same epitopes as those bound by ATN-615 and ATN-658. Such mimics of ATN-615 and ATN-658, the latter of which has particularly robust anti-tumor activity, are included herein as therapeutic and/or diagnostic agents.

The present invention is further directed to macromolecules, including Abs, antigen binding fragments such as single chain Abs=(scFv), non-Ab polypeptides and peptides, aptamers, etc., as well as small organic molecules, that have the property of binding to uPAR without inhibiting the binding of uPA. Some of these molecules interfere with downstream interactions of either uPA-uPAR or uPAR alone.

In addition to specific compositions that target uPA-uPAR interactions, this invention is also directed to methods for detecting Abs that bind exclusively to uPA-uPAR or that inhibit downstream interactions of uPAR. Thus, the invention includes a method for identifying these uPA-uPAR complex-binding molecules. This method may be varied to detect molecules that bind other components or complexes of the uPA/uPAR system. For example, uPA bound to its natural inhibitor PAI-1 also binds uPAR, forming a uPA:PAI-1/uPAR ternary complex. One method of the present invention comprises using such ternary complexes to screen for ligands which interact only with this complex but not with the binary uPA:PAI or uPA-uPAR complex. Another method is directed to inhibitors that interfere with the interaction of the ternary complexes with down-stream targets such as LRP.

Such an approach is suitable to identify ligand molecules that become internalized when bound to the complex.

In addition, this invention includes methods to detect a molecule that binds to the uPA-uPAR complex (but not to uncomplexed uPA or uPAR) or to detect inhibitors that interfere with the binding of uPA-uPAR or uPAR to downstream targets as well as the binding ligands themselves. Such binders may be Abs, others proteins, peptides, aptamers, small molecules, etc. A specific embodiment of this type would be a uPA-uPAR or uPAR ligand that interfered with uPAR mediated assembly of Fn or that perturbed the binding of Fn or Fn fragments to the integrin $\alpha_5\beta_1$. Alterations of the assembly of other matrix components (e.g., vitronectin) are also covered by this invention.

This invention is also directed to methods for identifying inhibitors of plasminogen activation that do not inhibit uPA catalytic activity and novel compositions that have this activity.

More specifically, the present invention is directed to a ligand that binds to a binary uPA-uPAR complex, which ligand does not substantially bind to (a) free uPA or (b) the region of uPAR that recognizes and binds to uPA, so that the ligand does not inhibit uPA-uPAR binding.

Another embodiment comprises a ligand that binds to a ternary complex of uPA-uPAR and an additional molecule (X), such as PAI-1, which ligand:
(a) binds to a uPA-uPAR-X complex,
(b) does not substantially bind to any of the following: (i) a uPA-uPAR complex, (ii) a uPA-X complex, (iii) the uPA-recognizing and uPA-binding region of uPAR or of X, (iv) free uPA, or (v), free X; and
(c) does not substantially inhibit uPA-uPAR binding or uPA-X binding.

Preferably, the above ligand substantially does not bind to free uPAR.

The above ligand may be a polypeptide, preferably an Ab, such as a mAb, or an antigen binding fragment thereof. Preferred mAbs are humanized chimeric or human mAbs.

In one embodiment, a preferred mAb or antigen-binding fragment comprises:
(a) a $V_L$ chain comprising three CDR's which have the respective amino acids sequences SEQ ID NO:3, SEQ ID NO:4 and SEQ ID NO:5; and
(b) a $V_H$ chain comprising three CDR's which have the respective amino acids sequences SEQ ID NO:6, SEQ ID NO:7 and SEQ ID NO:8.

A more preferred mAb or antigen binding fragment, as above, comprises
(a) a $V_L$ chain with the sequence SEQ ID NO: 1; and
(b) a $V_H$ chain with the sequence SEQ ID NO:2.

In another preferred embodiment, the mAb or antigen-binding fragment comprises:
(a) a $V_L$ chain comprising three CDR's which have the respective amino acids sequences SEQ ID NO:11, SEQ ID NO:12 and SEQ ID NO:13; and (b) a $V_H$ chain comprising three CDR's which have the respective amino acids sequences SEQ ID NO:14, SEQ ID NO:15 and SEQ ID NO:16.

A more preferred mAb or antigen binding fragment, as above, comprises:

(a) a $V_L$ chain has the sequence SEQ ID NO:9; and
(b) a $V_H$ chain has the sequence SEQ ID NO:10.

A preferred Ab of the present invention is one selected from: (a) mAb designated ATN-615 produced by hybridoma having ATCC Accession #PTA-8192; (b) a mAb designated ATN-658 produced by a hybridoma having ATCC Accession #PTA-8191; (c) a mAb having essentially the same antigen-binding characteristics as ATN-615; and (d) a mAb having essentially the same antigen-binding characteristics as ATN-658.

In one embodiment, the above ligand is one that inhibits binding of uPA-uPAR complexes with another biological ligand for these complexes. Examples of "other biological ligands" include integrins, preferably $\alpha 5\beta 1$, $\alpha v\beta 3$, $\alpha v\beta 5$, $\alpha 3\beta 1$, $\alpha 6\beta 1$, or $\alpha 4\beta 1$.

The above ligand may be one that ligand interferes with and inhibits (a) uPAR mediated assembly of Fn, (b) binding of Fn or a fragment thereof to integrin $\alpha_5\beta_1$, or (c) the assembly of Vn components.

In a preferred embodiment, the above ligand is (a) diagnostically labeled (with a detectable label); or (b) labeled with, conjugated to, or fused to (in the case of a polypeptide), a therapeutically active moiety, rendering the ligand therapeutically active.

Provided herein is a diagnostic composition comprising (a) the diagnostically labeled ligand as above; and (b) a diagnostically acceptable carrier.

In the diagnostic composition the ligand is preferably labeled with a radionuclide, a PET-imagable agent, an MRI-imagable agent, a fluorescer, a fluorogen, a chromophore, a chromogen, a phosphorescer, a chemiluminescer or a bioluminescer. Preferred radionuclides are selected from the group consisting of $^{3}H$, $^{14}C$, $^{35}S$, $^{67}Ga$, $^{68}Ga$, $^{72}As$, $^{89}Zr$, $^{97}Ru$, $^{99}Tc$, $^{111}In$, $^{123}I$, $^{125}I$, $^{131}I$, $^{169}Yb$ and $^{201}Tl$. Preferred fluorescers or fluorogens are fluorescein, rhodamine, dansyl, phycoerythrin, phycocyanin, allophycocyanin, o-phthaldehyde, fluorescamine, a fluorescein derivative, Oregon Green, Rhodamine Green, Rhodol Green and Texas Red.

The present invention provides a therapeutic anti-angiogenic or anti-tumor pharmaceutical composition that inhibits undesired angiogenesis, tumor growth and/or tumor metastasis comprising (a) an effective amount of the therapeutically active ligand above, and (b) a pharmaceutically acceptable carrier. This composition is preferably in a form suitable for injection. The therapeutically active moiety may be conjugated directly to, or bound indirectly to, the ligand. A preferred therapeutic moiety is a chemotherapeutic drug, a toxin or a therapeutic radionuclide (preferably $^{47}Sc$, $^{67}Cu$, $^{90}Y$, $^{109}Pd$, $^{125}I$, $^{131}I$, $^{186}Re$, $^{188}Re$, $^{199}Au$, $^{211}At$, $^{212}Pb$ or $^{217}Bi$).

In the above therapeutic composition, the therapeutically active moiety may be a peptide or polypeptide, e.g., a toxin, which is fused to the ligand.

This invention is directed to a method for inhibiting cell migration, cell invasion, cell proliferation or angiogenesis, or for inducing apoptosis, comprising contacting cells associated with undesired cell migration, invasion, proliferation or angiogenesis with an effective amount of the above therapeutically active ligand Also included is a method for treating a subject having a disease, disorder or condition characterized by undesired angiogenesis, tumor growth and/or tumor metastasis comprising administering to the subject an effective amount of the above therapeutic pharmaceutical composition.

Also provided is an assay method for detecting in a sample a substance suspected of having the binding properties of the above ligand, comprising (a) contacting the sample with uPA-uPAR complexes and determining binding of a component of the sample to the complexes;

(b) contacting the sample with free uPAR and determining binding of a component of the sample to the uPAR.

(c) comparing the binding of (a) and (b), wherein the presence of binding in (a) and a substantial absence or significantly lower binding in (b) is indicative of the present of the substance in the sample.

The assay may be a competitive binding assay using a labeled binding partner that binds to uPA-uPAR complexes, wherein the substance in the sample competes for binding with the binding partner.

One embodiment is an assay method for detecting in a sample a substance suspected of having the binding properties of the above ligand, comprising (a) contacting the sample with uPA-uPAR-X complexes (with X defined as above) and determining binding of a component of the sample to the complexes;

(b) contacting the sample with one or more of (i) uPA:X complexes; (ii) uPA-uPAR complexes; or (iii) uncomplexed X, and determining binding of a component of the sample to uPA-X, uPA-uPAR or X;

(c) comparing the binding of (a) and (b), wherein the presence of binding in (a) and a substantial absence or significantly lower binding in (b) is indicative of the present of the substance in the sample.

In the above method, the complexes may be on a cell surface

This invention includes an isolated peptide comprising at least 3 amino acids, which peptide, when part of a longer amino acid sequence, is present in a linear epitope bound by a mAb which has (a) a $V_L$ chain comprising three CDR's which have the respective amino acids sequences SEQ ID NO:3, SEQ ID NO:4 and SEQ ID NO:5; and (b) a $V_H$ chain comprising three CDR's which have the respective amino acids sequences SEQ ID NO:6, SEQ ID NO:7 and SEQ ID NO:8. A preferred isolated peptide as above is present in a linear epitope bound by a mAb with (A) a $V_L$ chain that has the sequence SEQ ID NO:1; and (b) a $V_H$ chain that has the sequence SEQ ID NO:2.

In another embodiment, the isolated peptide comprises at least 3 amino acids, and peptide, when it is part of a longer amino acid sequence, it is present in a linear epitope bound by a mAb having (a) a $V_L$ chain comprising three CDR's which have the respective amino acids sequences SEQ ID NO:11, SEQ ID NO:12 and SEQ ID NO:13; and (b) a $V_L$ chain comprising three CDR's which have the respective amino acids sequences SEQ ID NO:14, SEQ ID NO:15 and SEQ ID NO:16. A preferred isolated peptide as above is present in a linear epitope bound by a mAb having (a) a $V_L$ chain that has the sequence SEQ ID NO:9; and (b) a $V_H$ chain that has the sequence SEQ ID NO:10.

The invention is also directed to an isolated peptide, or a substitution variant thereof, comprising at least 3 amino acids, which peptide, when part of a longer amino acid sequence, is present in a linear epitope recognized by the mAb designated ATN-615 or by the mAb designated ATN-658.

The invention includes an assay method for identifying an Ab or other ligand that binds to the same epitope as does mAb ATN-615 or mAb ATN-658 comprising measuring the ability of a sample suspected of containing the Ab or other ligand to competitively inhibit the binding of detectably labeled ATN-615 or ATN-658 to (i) immobilized suPAR, (ii) immobilized suPAR D2D3 or (iii) an immobilized fragment of suPAR or D2D3 of suPAR, wherein competitive inhibition of at least about 20%, preferably 50%, more preferably 70% and most preferably 90%, indicates that an antibody or ligand binds to the same epitope.

One embodiment is a method for identifying a peptide that is recognized by (a) ATN-615, (b) ATN-658, or (c) an Ab or other ligand that with the same binding specificity as ATN-615 or ATN-658, which method comprises measuring the ability of a sample suspected of containing the peptide, or a candidate peptide, to competitively inhibit the binding of detectably labeled ATN-615 or ATN-658 or the Ab or other ligand with the same binding specificity, to (i) immobilized suPAR, (ii) immobilized suPAR D2D3 or (iii) an immobilized fragment of suPAR or D2D3 of suPAR, wherein competitive inhibition of at least about 20%, preferably 50%, more preferably 70% and most preferably 90%, indicates that the peptide has the binding specificity.

Included herein is an assay to screen for a compound, or to determine whether a candidate compound has essentially the same binding characteristics to a uPAR structure as does ATN-615 or ATN-658, comprising measuring the ability of a sample being screened or the candidate compound to competitively inhibit the binding of detectably labeled ATN-615 or ATN-658 to (i) immobilized suPAR, (ii) immobilized suPAR D2D3 or (iii) an immobilized fragment of suPAR or D2D3 of suPAR, wherein competitive inhibition of at least about 20%, preferably 50%, more preferably 70% and most preferably 90%, indicates that the peptide has the binding characteristics.

In one embodiment of the foregoing assay, the compound being screened for, or the candidate compound, is a small organic molecule having a molecular mass between about 50 Da and about 2500 Da. In another embodiment, the compound being screened for, or the candidate compound, is a nucleic acid molecule, preferably an oligonucleotide such as an RNAi molecule or an aptamer.

BRIEF DESCRIPTION OF THE DRAWINGS

FIGS. 10A and 10B both show results of a competition assay using biotin-labeled ATN-658 to identify mAbs that recognize the same epitope on suPAR. ATN-616 and ATN-617 are anti-uPAR antibodies that block the binding of uPA to uPAR. ATN-616 specifically binds ligand-occupied uPAR.

DESCRIPTION OF THE PREFERRED EMBODIMENTS

The present inventors have found that mabs, peptides or other chemical entities that target the uPA/uPAR complex or the uPAR-integrin complex are useful in the treatment and/or diagnosis of cancer. To date, the present inventors believe that no antibodies have been described that recognize the uPA-uPAR complex but not (a) uPAR or uPA individually or (b) uPAR in the presence of uPA (i.e., ligand occupied uPAR).

Further, the uPA-uPAR complex or uPAR alone have other "downstream" ligands such as integrins, low-density lipoprotein receptor-related protein (LRP) and other binding partners. These downstream interactions are believed to be important to the processes of cell migration, invasion and proliferation. It is thus desirable processes to target these processes therapeutically or detect the process or their interacting components diagnostically.

In addition to specific antibodies that target these interactions, as described in more detail below, this invention is also directed to methods for detecting antibodies that bind exclusively to the uPA-uPAR complex or that inhibit downstream interactions of uPAR.

The Antibody Approach

The present inventors have generated a panel of mAbs targeting uPAR. uPAR is an ideal target for antibodies because it is expressed on the cell surface. Expression of uPAR at the tumor-vasculature interface (on invasive tumor cells, angiogenic endothelial cells, or tumor-associated macrophages) suggests that antibodies targeting this protein would not suffer the same barriers to diffusion that have led to the failure of other mAbs to enter tumors and serve as diagnostic agents or exert therapeutic effects. Importantly, uPAR is not normally expressed on quiescent tissues, which should minimize the potential for toxicity when employing a therapeutic Ab and minimize non-specific signals (or false positives) when employing a diagnostic Ab.

Figure 2:
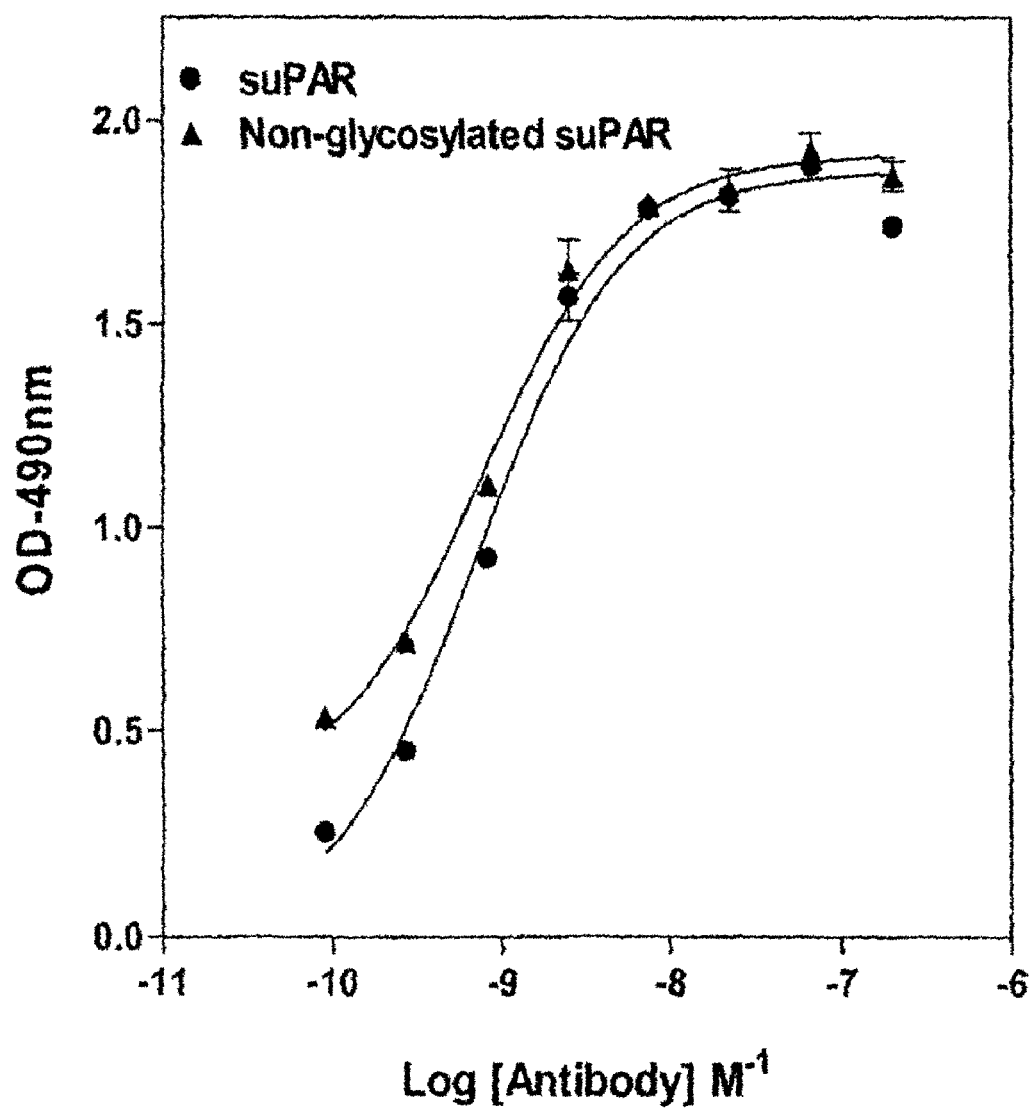
FIG. 2. ATN-658 binds to a non-glycosylated mutant of suPAR, indicating that ATN-658 is directed against a peptide (not a carbohydrate) epitope, like most other anti-uPAR mabs.

The present inventors have raised mAbs against a fragment of the soluble form of uPAR (known as "suPAR") expressed in *Drosophila* S2 cells. In such cells, a minimally glycosylated isotype of suPAR is expressed. Use of this suPAR as an immunogen is expected to overcome the heterogeneous binding to uPAR observed with all other mAbs examined to date. Studies performed as part of a Leukocyte Antigen Workshop compared anti-uPAR antibodies available in 1995-1996 and found all of them to be specific for carbohydrate, not protein, epitopes (Manupello, J. et al., (1996) *Tiss. Antigens* 48: 368). Indeed, uPAR expressed in tumors is highly and heterogeneously glycosylated, and the glycosylation pattern and representation of different isoforms change in response to various signals (Stoppelli M P et al. (1985) *Proc. Natl. Acad. Sci. USA* 82 4939-4943). Thus, anti-uPAR antibodies raised against carbohydrate epitopes are unlikely to recognize all isoforms of uPAR and may cross-react undesirably with other proteins expressing glycosylation structures similar to those present on uPAR. Use of S2 has led to the identification of mAbs that recognize the protein epitopes within suPAR (FIG. 2).

The present inventors have produced stable clones that express high amounts of suPAR as well as domain fragments of suPAR. Typical yields using these expression systems are on the order of 25-50 mgs/L after purification (>95% pure). Thus, the present inventors have shown that it is possible to express all the components required for the generation of the antibodies of the present invention and to design assays to evaluate and characterize them.

A mutant form of suPAR has been expressed in which all glycosylation sites have been mutated. The existing murine mAb clones may be humanized or primatized.

The present inventors' ability to generate conformationally intact domain fragments of suPAR has allowed them to produce mAbs against isolated D1 and isolated D2D3 (of suPAR). An epitope exposed in the uPAR D2D3 fragment is also exposed in full length, intact uPAR only after binding of uPA. This epitope has been demonstrated to be critical to the pro-migratory activity of uPA (Andolfo A et al. (2002) *Thromb Haemost* 88:298-306). Thus, antibodies generated against the D2D3 fragment where this epitope is already exposed, are expected to have anti-migratory activity. This has been demonstrated for mAbATN-658.

This invention is thus directed in part to a mAb that binds to a binary uPA-uPAR complex, but not substantially to (a) free uPA or (b) the region of uPAR that recognizes and binds to uPA, so that the mAb does not inhibit uPA-uPAR binding, which mAb is produced by a process comprising the initial step of immunizing a mammal, preferably a mouse, with
(a) a minimally glycosylated isotype of suPAR expressed in *Drosophila* cells, or
(b) a de-glycosylated mutant of suPAR in which 4 or 5 glycosylation sites have been mutated.

Following immunization using standard protocols, conventional techniques are employed to generate hybridoma cell lines from the immunized animals and to generate mAbs having the desired properties. mAbs specific for uPA-uPAR complexes having additional or somewhat different properties as disclosed herein are made in the same way using the same novel suPAR antigens. The mAbs made by this process may or may not bind free uPAR in solution.

There are five N-linked glycosylation sites in wild-type uPAR: $Asn^{52}$ (in D1) $Asn^{162}$ and $Asn^{172}$ (in D2) and $Asn^{200}$ and $Asn^{233}$ (in D3). The latter four sites in D2 and D3 are preferably mutated to Gln to generate a preferred de-glycosylated suPAR immunogen for raising mAbs of the invention.

Anti-D2D3 mAbs have also been generated which recognize uPAR on cell surfaces regardless of whether the uPAR is occupied by uPA. Since a large percentage of uPAR on tumors indeed is bound to uPA, antibodies of this specificity are useful as targeting agents for therapeutic and diagnostic moieties. In addition, in cancer patients, it is frequently observed that tumors express uPAR that is cleaved by proteases expressed by these same tumors, leaving a residual D2D3 fragment still attached to the tumor (Sier C F et al., Thromb Haemost. 2004, 91:403-11). Thus, successful targeting of these tumors require anti D2D3 antibodies. These antibodies are also useful for in vivo imaging applications.

The anti-D2D3 antibodies (and other antibodies of the present invention) are tested preferably in xenogeneic tumor models, two preferred examples of which are the A2780 and A549 models (described in more detail below).

Variable (V) Region Amino Acid Sequences of Two Preferred mAbs mAb ATN-658: Variable Region Sequences The consensus amino acid sequence (single-letter code) of the light chain variable region ($V_L$) and heavy chain variable region ($V_H$) polypeptides of mAb ATN-658 are shown below. cDNA was prepared from total RNA extracted from the hybridoma expressing ATN-658 and the variable regions were cloned, amplified and sequenced using standard techniques. The complementarity-determining regions (CDRs) for each variable region are highlighted (italic, bold, underscored)

ATN-658 $V_L$ Consensus Protein (SEQ ID NO:1):

```
  1   DIXLTQSPLT LSVTIGQPAS ISC***KSSQSLL DSDGKTYLN***W LLQRPGQSPK
 51   RLIY***LVSKLD S***GVPDRFTGS GSGTDFTLKI SRVEAEDLGV YYC***WQGTGFP***
101   LTFGAGTKLE LKL
```

ATN-658 $V_H$ Consensus Protein (SEQ ID NO:2)

```
  1   VQLQESGPEL VKTGASVKIS CKAS***GYSFTS YYMH***WVKQSH GKSLEWIG***EI***
 51   *NPYNGGASYN QKIKG*RATFT VDTSSRTAYM QFNSLTSEDS AVYYCAR*SIY*
101   *GHSVLDY*WGQ GTTVTVS
```

TABLE 1

Characteristics of CDRs of ATN-658 L and H Chains

| CDR* | No. of residues | Sequence[1] | SEQ ID NO: |
|---|---|---|---|
| CDR L1 | 16 | KSSQSLLDSDGKTYLN | 3 |
| CDR L2 | 7 | LVSKLDS | 4 |
| CDR L3 | 9 | WQGTHFPLT | 5 |
| CDR H1 | 10 | GYSFTSYYMH | 6 |
| CDR H2 | 17 | EINPYNGGASYNQKIKG | 7 |
| CDR H3 | 10 | SIYGHSVLDY | 8 |

*CDR-L1: first CDR of L chain; CDR-H2: $2^{nd}$ CDR of H chain, etc.

mAb ATN-615: Variable Region Sequences

Amino acid sequence (single-letter code) of the light chain ($V_L$) and heavy chain ($V_H$) variable regions of monoclonal antibody ATN-615. cDNA was prepared from total RNA extracted from the hybridoma expressing ATN-615 and the variable regions cloned, amplified and sequenced using standard techniques. The complementarity-determining regions (CDRs) for each variable region are highlighted in red.

ATN-615 $V_L$ Consensus Protein Sequence (SEQ ID NO:9)

```
1    DIVLTQSPDI TAASLGQKVT ITC SASSSVS YMH WYQQKSG TSPKPWIF EI
51   SKLAS GVPAR FSGSGSGTSY SLTISSMEAE DAAIYYC QQW NYPFT FGGGT
101  KLEIKR
```

ATN-615 $V_H$ Consensus Protein Sequence (SEQ ID NO:10)

```
1    VKLQQSGPEV VKPGASVKIS CKAS GYSFTN FYIH WVKQRP GQGLEWIG WI
51   FHGSDNTEYN EKFKD KATLT ADTSSSTAYM QLSSLTSEDS AVYFCAR WGP
101  HWYFDV WGQG TTVTVSS
```

TABLE 2

Characteristics of the CDRs of ATN-615

| CDR* | No. of residues | Sequence | SEQ ID NO: |
|---|---|---|---|
| CDRL1 | 10 | SASSSVSYMH | 11 |
| CDRL2 | 7 | EISKLAS | 12 |
| CDRL3 | 8 | QQWNYPFT | 13 |
| CDRH1 | 10 | GYSFTNFYIH | 14 |
| CDRH2 | 17 | WIFHGSDNTEYNEKFKD | 15 |
| CDRH3 | 9 | WGPHWYFDV | 16 |

*CDR-L1: first CDR of L chain; CDR-H2: $2^{nd}$ CDR of H chain, etc.

According to the present invention, an Ab or mAb, has "essentially the same antigen-binding characteristics" as a reference mAb if it demonstrates a similar specificity profile (e.g., by rank order comparison), and has affinity for the relevant antigen (e.g., uPA-uPAR complex) within 1.5 orders of magnitude, more preferably within one order of magnitude, of the reference Ab.

The antibodies are evaluated for direct anti-angiogenic activity in an in vivo Matrigel plug model. Radioiodinated antibodies are used to test Ab internalization using in MDA MB 231 cells which express both receptor and ligand. Antibody internalization is also measured in the presence of PAI-1:uPA complexes.

Antibodies Specific for uPA, uPAR and Binary and Ternary Complexes Thereof

In the following description, reference will be made to various methodologies known to those of skill in the art of immunology, cell biology, and molecular biology. Publications and other materials setting forth such known methodologies to which reference is made are incorporated herein by reference in their entireties as though set forth in full. Standard reference works setting forth the general principles of immunology include Abbas, A K et al., *Cellular and Molecular Immunology* (Fourth Ed.), W.B. Saunders Co., Philadelphia, 2000; Janeway, C A et al., *Immunobiology. The Immune System in Health and Disease*, 4th ed., Garland Publishing Co., New York, 1999; Roitt, I et al., *Immunology*, (current ed.) C. V. Mosby Co., St. Louis, Mo. (1999); Klein, J, *Immunology*, Blackwell Scientific Publications, Inc., Cambridge, Mass., (1990).

Monoclonal antibodies (mAbs) and methods for their production and use are described in Kohler and Milstein, *Nature* 256:495-497 (1975); U.S. Pat. No. 4,376,110; Hartlow, E. et al., *Antibodies: A Laboratory Manual*, Cold Spring Harbor Laboratory Press, Cold Spring Harbor, N.Y., 1988); *Monoclonal Antibodies and Hybridomas: A New Dimension in Biological Analyses*, Plenum Press, New York, N.Y. (1980); H. Zola et al., in *Monoclonal Hybridoma Antibodies: Techniques and Applications*, CRC Press, 1982)).

Immunoassay methods are also described in Coligan, J E et al., eds., *Current Protocols in Immunology*, Wiley-Interscience, New York 1991 (or current edition); Butt, W R (ed.) *Practical Immunoassay: The State of the Art*, Dekker, New York, 1984; Bizollon, C A, ed., *Monoclonal Antibodies and New Trends in Immunoassays*, Elsevier, N.Y., 1984; Butler, J E, ELISA (Chapter 29), In: van Oss, C J et al., (eds), *IMMUNOCHEMISTRY*, Marcel Dekker, Inc., New York, 1994, pp. 759-803; Butler, J E (ed.), *Immunochemistry of Solid-Phase Immunoassay*, CRC Press, Boca Raton, 1991; Weintraub, B, *Principles of Radioimmunoassays*, The Endocrine Society, March, 1986; Work, T S et al., *Laboratory Techniques and Biochemistry in Molecular Biology*, North Holland Publishing Company, NY, 1978; Dabbs, D J, *Diagnostic Immunohistochemistry*, Churchill Livingstone, 2001.

Anti-idiotypic antibodies are described, for example, in *Idiotypy in Biology and Medicine*, Academic Press, New York, 1984; *Immunological Reviews* Vol. 79, 1984 and Vol. 90, 1986; *Curr. Top. Microbiol., Immunol*. Vol. 119, 1985; Bona, C. et al., *CRC Crit. Rev. Immunol.*, pp. 33-81 (1981);

Jerne, N K, *Ann. Immunol.* 125C:373-389 (1974); Urbain, J et al., *Ann. Immunol.* 133D:179-(1982); Rajewsky, K. et al., *Ann. Rev. Immunol.* 1:569-607 (1983).

The present invention provides antibodies, both polyclonal and monoclonal, reactive with uPA/uPAR complexes that inhibit interactions of uPAR with integrins or other downstream targets. The antibodies may be xenogeneic, allogeneic, syngeneic, or modified forms thereof, such as humanized or chimeric antibodies. Antiidiotypic antibodies specific for the idiotype of, for example, an anti-uPA/uPAR Ab are also included. The term "antibody" is also meant to include both intact molecules as well as fragments thereof that include the antigen-binding site and are capable of binding to a target epitope of, e.g., uPA/uPAR or uPAR-integrin complex. These include, Fab and F(ab')$_2$ fragments which lack the Fc fragment of an intact Ab, clear more rapidly from the circulation, and may have less non-specific tissue binding than an intact Ab (Wahl et al., *J. Nucl. Med.* 24:316-325 (1983)). Also included are Fv fragments (Hochman, J. et al. (1973) *Biochemistry* 12:1130-1135; Sharon, J. et al. (1976) Biochemistry 15:1591-1594)). These various fragments are produced using conventional techniques such as protease cleavage or chemical cleavage (see, e.g., Rousseaux et al., *Meth. Enzymol.*, 121:663-69 (1986))

Polyclonal antibodies are obtained as sera from immunized animals such as rabbits, goats, rodents, etc. and may be used directly without further treatment or may be subjected to conventional enrichment or purification methods such as ammonium sulfate precipitation, ion exchange chromatography, and affinity chromatography (see Zola et al., supra).

An immunogen for generation of the antibodies of this invention may comprise uPAR, suPAR, uPA/uPAR or uPAR-integrin complexes/or an epitope-bearing fragments or derivative thereof. Useful immunogens are produced in a variety of ways known in the art, e.g., expression of cloned genes using conventional recombinant methods, isolation from cells of origin, cell populations expressing high levels of e.g., uPA or uPAR, etc. In the case of shorter fragments, they may be chemically synthesized. A preferred immunogen is the D2D3 fragment of suPAR.

The mAbs may be produced using conventional hybridoma technology, such as the procedures introduced by Kohler and Milstein (*Nature*, 256:495-97 (1975)),—and modifications thereof (see above references). An animal, preferably a mouse is primed by immunization with an immunogen as above to elicit the desired Ab response in the primed animal.

B lymphocytes from the lymph nodes, spleens or peripheral blood of a primed, animal are fused with myeloma cells, generally in the presence of a fusion promoting agent such as polyethylene glycol (PEG). Any of a number of murine myeloma cell lines are available for such use: the P3-NS1/1-Ag4-1, P3-x63-k0Ag8.653, Sp2/0-Ag14, or HL1-653 myeloma lines (available from the ATCC, Rockville, Md.). Subsequent steps include growth in selective medium so that unfused parental myeloma cells and donor lymphocyte cells eventually die while only the hybridoma cells survive. These are cloned and grown and their supernatants screened for the presence of Ab of the desired specificity, e.g., by immunoassay techniques. Positive clones are subcloned, e.g., by limiting dilution, and the mAbs are isolated.

Hybridomas produced according to these methods can be propagated in vitro or in vivo (in ascites fluid) using techniques known in the art (see generally Fink et al., *Prog. Clin. Pathol.*, 9:121-33 (1984)). Generally, the individual cell line is propagated in culture and the culture medium containing high concentrations of a single mAb can be harvested by decantation, filtration, or centrifugation.

Production of mAbs

A preferred approach for producing a mAb according to the present invention is as follows. D2D3 is prepared from suPAR using chymotryptic digest and purification (Shliom, O. et al., (2000) *J. Biol. Chem.* 275:24304-12). D2D3 is then conjugated to any useful carrier protein such as albumin, keyhole limpet hemocyanin (KLH) or ovalbumin. Immunizations are typically carried out in complete Freund's adjuvant followed by periodic boosts in incomplete Freund's adjuvant. Animals are also bled periodically and the titer of the serum measured using an ELISA in which suPAR is immobilized to the surface of microplate wells.

If a peptide is used, it is preferably conjugated to a carrier protein, e.g., KLH, is and injected into BALB/c mice intraperitoneally (i.p.) in complete Freund's adjuvant (e.g., 50 µg conjugate), followed by two additional injections of the same dose in incomplete Freund's adjuvant at two week intervals. After one month, a final injection is given i.p (e.g., 50 µg in 0.5 ml PBS) and preferably also intravenously (i.v.) (e.g., 50 µg in 0.2 ml) without adjuvant.

Spleen cells are harvested three days after the final injection and fused with P3X63AF8/653 or other myeloma cells using standard techniques.

Test Cells for Screening and Characterizing Antibodies

Pure suPAR immobilized onto plastic is preferred for the primary screening. Cells such as the HeLa line that overexpress uPAR may also be used to demonstrate cell binding of an anti-suPAR mAb. Many tumor cell lines overexpressing uPAR are well-known and publicly available; these may be used for screening. Cells are generally plated in 96-well microplates. The cells may be fixed, e.g., with methanol/acetone (50/50), and the binding detected by immunofluorescence staining. Alternatively, the mAbs may be radiolabeled and binding detected by measurement of radioactivity.

In one embodiment, a hybridoma supernatant (e.g., 50 µl) is added to wells containing fixed 293 cells for about 1.5 h at 37° C. Plates are washed twice in washing buffer (such as PBS/0.05% Tween-20), and Rhodamine Red-conjugated goat anti-mouse IgG is added (e.g., 30 µl/well) at an appropriate dilution, such as 1:100, for 1.5 h at 37° C. After washing in a washing buffer, cells are examined for the presence of immunofluorescence; in the embodiment described here, fluorescence microscopy is used.

In this embodiment, immunofluorescence is the basis for determining whether a hybridoma supernatant contains an Ab specific for the uPA/uPAR complex (although immunohistochemical staining may also be used). If supernatants show positively staining the hybridoma clones are selected, expanded and the supernatants tested for reactivity to the complex by ELISA.

In a preferred ELISA, the peptide is coupled to ovalbumin (OVA) as a carrier protein and the peptide/OVA conjugate coated onto wells of 96 well EIA plate which receives, for example, 2 µg/ml of conjugate in 50 µl coating buffer (0.2 M Na$_2$CO$_3$/NaHCO$_3$, pH9.6). Plates are incubated overnight at 4° C., blocked with an appropriate blocking buffer, e.g., PBS containing 1% BSA (200 µl/well) overnight at 4° C. Hybridoma supernatants (e.g., 50 µl) are added to wells for 1.5 hours at room temperature. Plates are washed twice in washing buffer (e.g., PBS/0.05% Tween-20), and enzyme-coupled secondary Ab, such as alkaline phosphatase-coupled goat-anti-mouse IgG is added (50 µl/well) at an appropriate dilution, e.g., 1:2000. Plates are incubated for 1.5 hours at RT. After washing 4× in washing buffer, an appropriate chromogenic substrate for the enzyme, e.g., CP-nitrophenylphosphate in this embodiment (available from Kirkegaard and Perry Co., Gaithersburg, Md.), is added for about 30 min and absorbance measured at wavelength appropriate for the colored product (here 405 nm). Hybridoma supernatants that react strong with the epitope-bearing peptide (e.g., $A_{405}$>1.0 when negative controls are <0.02) are re-cloned (preferably twice), and the mab reactivity again confirmed by ELISA as above.

The term "antibody" is meant to include both intact immunoglobulin (Ig) molecules as well as fragments and derivative thereof, that may be produced by proteolytic cleavage of Ig molecules or engineered genetically or chemically. Fragments include, for example, Fab, Fab', F(ab')$_2$ and Fv, each of which is capable of binding antigen. These fragments lack the Fc fragment of intact Ab and have an additional advantage, if used therapeutically, of clearing more rapidly from the circulation and undergoing less non-specific tissue binding than intact antibodies. Papain treatment of Ig's produces Fab fragments; pepsin treatment produces F(ab')$_2$ fragments. These fragments may also produced by genetic or protein engineering using methods well known in the art. A Fab fragment is a multimeric protein consisting of the portion of an Ig molecule containing the immunologically active portions of an Ig heavy (H) chain and an Ig light (L) chain covalently coupled together and capable of specifically combining with antigen. Fab fragments are typically prepared by proteolytic digestion of substantially intact Ig molecules with papain using methods that are well known in the art. However, a Fab fragment may also be prepared by expressing in a suitable host cell the desired portions of Ig H chain and L chain using methods well known in the art. A (Fab')$_2$ fragment is a tetramer that includes a fragment of two H and two L chains. The Fv fragment is a multimeric protein consisting of the immunologically active portions of an Ig H chain variable (V) region ($V_H$) and an Ig L chain V region ($V_L$) covalently coupled together and capable of specifically combining with antigen. Fv fragments are typically prepared by expressing in suitable host cell the desired portions of Ig $V_H$ region and $V_L$ region using methods well known in the art.

Single-chain antigen-binding protein or single chain Ab, also referred to as "scFv," is a polypeptide composed of an Ig $V_L$ amino acid sequence tethered to an Ig $V_H$ amino acid sequence by a peptide that links the C-terminus of the $V_L$ sequence to the N-terminus of the $V_H$ sequence.

In a preferred embodiment, the Ab is a mAb designated ATN-615 or ATN-658, both of which are IgG1 antibodies.

In another preferred embodiment, the Ab is a chimeric Ab that recognizes an epitope recognized by ATN-615 or ATN-658.

Chimeric Antibodies

The chimeric antibodies of the invention comprise individual chimeric H and L Ig chains. The chimeric H chain comprises an antigen binding region derived from the H chain of a non-human Ab specific for e.g., uPA/uPAR or uPAR-integrin complex, for example, mAb ATN-615 or ATN-658, which is linked to at least a portion of a human $C_H$ region. A chimeric L chain comprises an antigen binding region derived from the L chain of a non-human Ab specific for the target antigen, such as the hybridoma ATN-615 or ATN-658, linked to at least a portion of a human $C_L$ region. As used herein, the term "antigen binding region" refers to that portion of an Ab molecule which contains the amino acid residues that interact with an antigen and confer on the Ab its specificity and affinity for the antigen. The Ab region includes the "framework" amino acid residues necessary to maintain the proper conformation of the antigen-binding (or "contact") residues.

As used herein, the term "chimeric antibody" includes monovalent, divalent or polyvalent Igs. A monovalent chimeric Ab is an HL dimer formed by a chimeric H chain associated through disulfide bridges with a chimeric L chain. A divalent chimeric Ab is tetramer $H_2L_2$ formed by two HL dimers associated through at least one disulfide bridge. A polyvalent chimeric Ab can also be produced, for example, by employing a $C_H$ region that aggregates (e.g., from an IgM H chain, termed the μ chain).

The invention also provides for "derivatives" of the mouse mAbs or the chimeric Abs, which term includes those proteins encoded by truncated or modified genes to yield molecular species functionally resembling the Ig fragments. The modifications include, but are not limited to, addition of genetic sequences coding for cytotoxic proteins such as plant and bacterial toxins. The fragments and derivatives can be produced from any of the hosts of this invention.

Antibodies, fragments or derivatives having chimeric H chains and L chains of the same or different V region binding specificity, can be prepared by appropriate association of the individual polypeptide chains, as taught, for example by Sears et al., *Proc. Natl. Acad. Sci. USA* 72:353-357 (1975). With this approach, hosts expressing chimeric H chains (or their derivatives) are separately cultured from hosts expressing chimeric L chains (or their derivatives), and the Ig chains are separately recovered and then associated. Alternatively, the hosts can be co-cultured and the chains allowed to associate spontaneously in the culture medium, followed by recovery of the assembled Ig, fragment or derivative.

The antigen binding region of the chimeric Ab (or a human mAb) of the present invention is derived preferably from a non-human Ab specific for e.g., uPA/uPAR or uPAR-integrin complex. Preferred sources for the DNA encoding such a non-human Ab include cell lines which produce Ab, preferably hybridomas. Preferred hybridomas are the ATN-615 hybridoma cell line (ATCC Accession No. PTA-8192) and ATN-658 (ATCC Accession No. PTA-8191) which were produced as described above and whose V regions have the sequences shown above.

Thus, a preferred chimeric Ab (or human Ab) has a $V_L$ sequence SEQ ID NO:1 and a $V_H$ sequence SEQ ID NO:2 which are the consensus sequences of mAb ATN-658. The residues of these V regions that are not in the CDR regions may be varied, preferably as conservative substitutions, as long as the V region results in an Ab with the same antigen-specificity and substantially the same antigen-binding affinity or avidity, preferably at least 20% of the affinity or avidity of an Ab wherein the $V_L$ sequence is SEQ ID NO:1 and the $V_H$ sequence is SEQ ID NO:2. It is preferred that in this chimeric (or human) Ab, the three CDR regions of the $V_L$ chain are SEQ ID NO:3, 4 and 5 and the three CDR regions of the $V_H$ chain are SEQ ID NO:6, 7 and 8.

Another preferred chimeric Ab (or human Ab) has a $V_L$ sequence SEQ ID NO:9 and a $V_H$ sequence SEQ ID NO:10 which are the consensus sequences of mAb ATN-615. The residues of these V regions that are not in the CDR regions may be varied, preferably as conservative substitutions, as long as the V region results in an Ab with the same antigen-specificity and substantially the same antigen-binding affinity or avidity, preferably at least 20% of the affinity or avidity of an Ab wherein the $V_L$ sequence is SEQ ID NO:9 and the $V_H$ sequence is SEQ ID NO:10. It is preferred that in this chimeric Ab, the three CDR regions of the $V_L$ chain are SEQ ID NO:11, 12 and 13 and the three CDR regions of the $V_H$ chain are SEQ ID NO:14, 15 and 16.

Preferred nucleic acid molecules for use in constructing a chimeric Ab (or human Ab) of this invention are (a) a nucleic acid molecule with a coding sequence that encodes a $V_L$ region with the sequence SEQ ID NO:1 and (b) a nucleic acid molecule with a coding sequence that encodes a $V_H$ chain with the sequence SEQ ID NO:2. Also preferred is a nucleic acid molecule that encodes a $V_L$ region comprising the three CDRs SEQ ID NO:3, 4 and 5 and a nucleic acid molecule that encodes a $V_H$ region comprising the three CDRs SEQ ID NO:6, 7 and 8.

Another set of preferred nucleic acid molecules for use in constructing a chimeric Ab (or human Ab) of this invention are (a) a nucleic acid molecule with a coding sequence that encodes a $V_L$ region with the sequence SEQ ID NO:9 and (b) a nucleic acid molecule with a coding sequence that encodes a $V_H$ chain with the sequence SEQ ID NO:10. Also preferred is a nucleic acid molecule that encodes a $V_L$ region comprising the three CDRs SEQ ID NO:11, 12 and 13 and a nucleic acid molecule that encodes a $V_H$ region comprising the three CDRs SEQ ID NO:14, 15 and 16.

Alternatively, the non-human Ab producing cell from which the V region of the Ab of the invention is derived may be a B lymphocyte obtained from the blood, spleen, lymph nodes or other tissue of an animal immunized with D2D3 of suPAR. The Ab-producing cell contributing the nucleotide sequences encoding the antigen-binding region of the chimeric Ab of the present invention may also be produced by transformation of a non-human, such as a primate, or a human cell. For example, a B lymphocyte which produces an Ab specific, e.g., uPA/uPAR or uPAR-integrin complex may be infected and transformed with a virus such as Epstein-Barr virus to yield an immortal Ab producing cell (Kozbor et al. *Immunol. Today* 4:72-79 (1983)). Alternatively, the B lymphocyte may be transformed by providing a transforming gene or transforming gene product, as is well-known in the art. Preferably, the antigen binding region will be of murine origin. In other embodiments, the antigen binding region may be derived from other animal species, in particular rodents such as rat or hamster.

The murine or chimeric mAb of the present invention may be produced in large quantities by injecting hybridoma or transfectoma cells secreting the Ab into the peritoneal cavity of mice and, after appropriate time, harvesting the ascites fluid which contains a high titer of the mAb, and isolating the mAb therefrom. For such in vivo production of the mab with a non-murine hybridoma (e.g., rat or human), hybridoma cells are preferably grown in irradiated or athymic nude mice.

Alternatively, the antibodies may be produced by culturing hybridoma (or transfectoma) cells in vitro and isolating secreted mAb from the cell culture medium.

Human genes which encode the constant C regions of the chimeric antibodies of the present invention may be derived from a human fetal liver library or from any human cell including those which express and produce human Igs. The human $C_H$ region can be derived from any of the known classes or isotypes of human H chains, including γ, μ, α, δ or ε, and subtypes thereof, such as G1, G2, G3 and G4. Since the H chain isotype is responsible for the various effector functions of an Ab, the choice of $C_H$ region will be guided by the desired effector functions, such as complement fixation, or activity in Ab-dependent cellular cytotoxicity (ADCC). Preferably, the $C_H$ region is derived from γ1 (IgG1), γ3 (IgG3), γ4 (IgG4), or μ (IgM).

The human $C_L$ region can be derived from either human L chain isotype, κ or λ.

Genes encoding human Ig C regions are obtained from human cells by standard cloning techniques (Sambrook, J. et al., *Molecular Cloning: A Laboratory Manual,* 2nd Edition, Cold Spring Harbor Press, Cold Spring Harbor, N.Y. (1989)). Human C region genes are readily available from known clones containing genes representing the two classes of L chains, the five classes of H chains and subclasses thereof.

Chimeric Ab fragments, such as F(ab')$_2$ and Fab, can be prepared by designing a chimeric H chain gene which is appropriately truncated. For example, a chimeric gene encoding an H chain portion of an F(ab')$_2$ fragment would include DNA sequences encoding the $CH_1$ domain and hinge region of the H chain, followed by a translational stop codon to yield the truncated molecule.

Generally, the chimeric antibodies of the present invention are produced by cloning DNA segments encoding the H and L chain antigen-binding regions of a specific Ab of the invention, preferably non-human, and joining these DNA segments to DNA segments encoding human $C_H$ and $C_L$ regions, respectively, to produce chimeric Ig-encoding genes.

Thus, in a preferred embodiment, a fused gene is created which comprises a first DNA segment that encodes at least the antigen-binding region of non-human origin, such as a functionally rearranged V region with joining (J) segment, linked to a second DNA segment encoding at least a part of a human C region.

The DNA encoding the Ab-binding region may be genomic DNA or cDNA. A convenient alternative to the use of chromosomal gene fragments as the source of DNA encoding the murine V region antigen-binding segment is the use of cDNA for the construction of chimeric Ig genes, as reported by Liu et al. (*Proc. Natl. Acad. Sci., USA* 84:3439 (1987); *J. Immuno.* 139:3521 (1987), which references are hereby incorporated by reference. The use of cDNA requires that gene expression elements appropriate for the host cell be combined with the gene in order to achieve synthesis of the desired protein. The use of cDNA sequences is advantageous over genomic sequences (which contain introns), in that cDNA sequences can be expressed in bacteria or other hosts which lack appropriate RNA splicing systems.

Therefore, in an embodiment utilizing cDNA encoding the Ab V region, the method of producing the chimeric Ab involves several steps, outlined below:

1. Isolation of messenger RNA (mRNA) from the cell line producing the mAb, cloning and cDNA production therefrom;
2. Preparation of a full length cDNA library from purified mRNA from which the appropriate V region gene segments of the L and H chain genes can be: (i) identified with appropriate probes, (ii) sequenced, and (iii) made compatible with a C gene segment;
3. Preparation of C region gene segments by cDNA preparation and cloning;
4. Construction of complete H or L chain coding sequences by linkage of the cloned specific V region gene segments to cloned human C region gene, as described above;
5. Expression and production of chimeric L and H chains in selected hosts, including prokaryotic and eukaryotic cells.

One common feature of all Ig H and L chain genes and their encoded mRNAs is the J region. H and L chain J regions have different sequences, but a high degree of sequence homology exists (greater than 80%) among each group, especially near the C region. This homology is exploited in this method and consensus sequences of H and L chain J regions may be used to design oligonucleotides for use as primers for introducing useful restriction sites into the J region for subsequent linkage of V region segments to human C region segments.

C region cDNA vectors prepared from human cells can be modified by site-directed mutagenesis to place a restriction site at the analogous position in the human sequence. For example, one can clone the complete human κ chain C ($C_k$) region and the complete human γ-1 C region ($C_{\gamma-1}$). In this case, the alternative method based upon genomic C region clones as the source for C region vectors would not allow these genes to be expressed in bacterial systems where enzymes needed to remove intervening sequences are absent. Cloned V region segments are excised and ligated to L or H chain C region vectors. Alternatively, the human $C_{\gamma-1}$ region can be modified by introducing a termination codon thereby generating a gene sequence which encodes the H chain portion of a Fab molecule. The coding sequences with linked V and C regions are then transferred into appropriate expression vehicles for expression in appropriate hosts, prokaryotic or eukaryotic.

Two coding DNA sequences are said to be "operably linked" if the linkage results in a continuously translatable sequence without alteration or interruption of the triplet reading frame. A DNA coding sequence is operably linked to a gene expression element if the linkage results in the proper function of that gene expression element to result in expression of the coding sequence.

Expression vehicles include plasmids or other vectors. Preferred among these are vehicles carrying a functionally complete human $C_H$ or $C_L$ chain sequence having appropriate restriction sites engineered so that any $V_H$ or $V_L$ chain sequence with appropriate cohesive ends can be easily inserted therein. Human $C_H$ or $C_L$ chain sequence-containing vehicles thus serve as intermediates for the expression of any desired complete H or L chain in any appropriate host.

A chimeric mouse-human Ab will typically be synthesized from genes driven by the chromosomal gene promoters native to the mouse H and L chain V regions used in the constructs. Splicing usually occurs between the splice donor site in the mouse J region and the splice acceptor site preceding the human C region and also at the splice regions that occur within the human $C_H$ region; polyadenylation and transcription termination occur at native chromosomal sites downstream of the human coding regions.

Gene expression elements useful for the expression of cDNA genes include: (a) viral transcription promoters and their enhancer elements, such as the SV40 early promoter (Okayama, H. et al., *Mol. Cell. Biol.* 3:280 (1983)), Rous sarcoma virus LTR (Gorman, C. et al., *Proc. Natl. Acad. Sci., USA* 79:6777 (1982)), and Moloney murine leukemia virus LTR (Grosschedl, R et al., *Cell* 41:885 (1985)); (b) splice regions and polyadenylation sites such as those derived from the SV40 late region (Okayama et al., supra); and (c) polyadenylation sites such as in SV40 (Okayama et al., supra).

Ig cDNA genes may be expressed as described by Liu et al., supra, and Weidle, U H et al., *Gene* 51:21-29 (1987), using as expression elements the SV40 early promoter and its enhancer, the mouse Ig H chain promoter enhancers, SV40 late region mRNA splicing, rabbit β-globin intervening sequence, Ig and rabbit β-globin polyadenylation sites, and SV40 polyadenylation elements. For Ig genes comprised of part cDNA, part genomic DNA (Whittle, N et al., *Protein Eng.* 1:499-505 (1987)), the transcriptional promoter is human cytomegalovirus, the promoter enhancers are cytomegalovirus and mouse/human Ig, and mRNA splicing and polyadenylation regions are from the native chromosomal Ig sequences. In one embodiment, for expression of cDNA genes in rodent cells, the transcriptional promoter is a viral LTR sequence, the transcriptional promoter enhancers are either or both the mouse Ig H chain enhancer and the viral LTR enhancer, the splice region contains an intron of greater than 31 bp, and the polyadenylation and transcription termination regions are derived from the native chromosomal sequence corresponding to the Ig chain being synthesized. In other embodiments, cDNA sequences encoding other proteins are combined with the above-recited expression elements to achieve expression of the proteins in mammalian cells.

Each fused gene is assembled in, or inserted into, an expression vector. Recipient cells capable of expressing the chimeric Ig chain gene product are then transfected singly with a chimeric H or chimeric L chain-encoding gene, or are co-transfected with a chimeric H and a chimeric L chain gene. The transfected recipient cells are cultured under conditions that permit expression of the incorporated genes and the expressed Ig chains or intact antibodies or fragments are recovered from the culture. In one embodiment, the fused genes encoding the chimeric H and L chains, or portions thereof, are assembled in separate expression vectors that are then used to co-transfect a recipient cell.

Each vector may contain two selectable genes, a first selectable gene designed for selection in a bacterial system and a second selectable gene designed for selection in a eukaryotic system, wherein each vector has a different pair of genes. This strategy results in vectors which first direct the production, and permit amplification, of the fused genes in a bacterial system. The genes so produced and amplified in a bacterial host are subsequently used to co-transfect a eukaryotic cell, and allow selection of a co-transfected cell carrying the desired transfected genes. Examples of selectable genes for use in a bacterial system are the gene that confers resistance to ampicillin and the gene that confers resistance to chloramphenicol. Preferred selectable genes for use in eukaryotic transfectants include the xanthine guanine phosphoribosyl transferase gene (designated gpt) and the phosphotransferase gene from Tn5 (designated neo).

Selection of cells expressing gpt is based on the fact that the enzyme encoded by this gene utilizes xanthine as a substrate for purine nucleotide synthesis, whereas the analogous endogenous enzyme cannot. In a medium containing (1) mycophenolic acid, which blocks the conversion of inosine monophosphate to xanthine monophosphate (XMP), and (2) xanthine, only cells expressing the gpt gene can survive. The product of the neo gene blocks the inhibition of protein synthesis by the antibiotic G418 and other antibiotics of the neomycin class.

The two selection procedures can be used simultaneously or sequentially to select for the expression of Ig chain genes introduced on two different DNA vectors into a eukaryotic cell. It is not necessary to include different selectable markers for eukaryotic cells; an H and an L chain vector, each containing the same selectable marker can be co-transfected. After selection of the appropriately resistant cells, the majority of the clones will contain integrated copies of both H and L chain vectors.

Alternatively, the fused genes encoding the chimeric H and L chains can be assembled on the same expression vector.

For transfection of the expression vectors and production of the chimeric Ab, the preferred recipient cell line is a myeloma cell. Myeloma cells can synthesize, assemble and secrete Igs encoded by transfected Ig genes and possess the mechanism for glycosylation of the Ig. A particularly preferred recipient cell is the Ig-non-producing myeloma cell SP2/0 (ATCC #CRL 8287). SP2/0 cells produce only Ig encoded by the transfected genes. Myeloma cells can be grown in culture or in the peritoneal cavity of a mouse, where secreted Ig can be obtained from ascites fluid. Other suitable recipient cells include lymphoid cells such as B lymphocytes of human or non-human origin, hybridoma cells of human or non-human origin, or interspecies heterohybridoma cells.

The expression vector carrying a chimeric Ab construct of the present invention may be introduced into an appropriate host cell by any of a variety of suitable means, including such biochemical means as transformation, transfection, conjugation, protoplast fusion, calcium phosphate-precipitation, and application with polycations such as diethylaminoethyl (DEAE) dextran, and such mechanical means as electroporation, direct microinjection, and microprojectile bombardment.

The chimeric Ig coding sequences or genes of the present invention can also be expressed in nonlymphoid mammalian cells or in other eukaryotic cells, such as yeast, or in prokaryotic cells, in particular bacteria. Yeast provides substantial advantages over bacteria for the production of Ig H and L chains. Yeasts carry out post-translational peptide modifications including glycosylation. A number of recombinant DNA strategies now exist which utilize strong promoter sequences and high copy number plasmids which can be used for production of the desired proteins in yeast. Yeast recognizes leader sequences of cloned mammalian gene products and secretes peptides bearing leader sequences (i.e., pre-peptides). Yeast gene expression systems can be routinely evaluated for the levels of production, secretion and the stability of chimeric H and L chain proteins and assembled chimeric Abs. Any of a series of yeast gene expression systems incorporating promoter and termination elements from the actively expressed genes coding for glycolytic enzymes produced in large quantities when yeasts are grown in media rich in glucose can be utilized. Known glycolytic genes can also provide very efficient transcription control signals. For example, the promoter and terminator signals of the phosphoglycerate kinase (PGK) gene can be utilized. A number of approaches may be taken for evaluating optimal expression plasmids for the expression of cloned Ig cDNAs in yeast (see Glover, D. M., ed., *DNA Cloning*, IRL Press, 1985).

Bacterial strains may also be utilized as hosts for the production of Ab molecules or Ab fragments described by this invention, *E. coli* K12 strains such as *E. coli* W3110 (ATCC# 27325), and other enterobacteria such as *Salmonella typhimurium* or *Serratia marcescens*, and various *Pseudomonas* species may be used.

Plasmid vectors containing replicon and control sequences which are derived from species compatible with a host cell are used in connection with these bacterial hosts. The vector carries a replication site, as well as specific genes which are capable of providing phenotypic selection in transformed cells. A number of approaches may be taken for evaluating the expression plasmids for the production of chimeric Abs or Ab chains encoded by the cloned Ig cDNAs in bacteria (see Glover, supra).

Preferred hosts are mammalian cells, grown in vitro or in vivo. Mammalian cells provide post-translational modifications to Ig protein molecules including leader peptide removal, folding and assembly of H and L chains, glycosylation of the Ab molecules, and secretion of functional Ab protein. Mammalian cells which may be useful as hosts for the production of Ab proteins, in addition to the cells of lymphoid origin described above, include cells of fibroblast origin, such as Vero (ATCC CRL 81) or CHO-K1 (ATCC CRL 61). Many vector systems are available for the expression of cloned H and L chain genes in mammalian cells (see Glover, supra). Different approaches can be followed to obtain complete $H_2L_2$ Abs.

For in vivo use, particularly for injection into humans, it is desirable to decrease the immunogenicity of the mAb by making mouse-human (or rodent-human) chimeric Abs as above, or by humanizing the Abs using methods known in the art. The humanized Ab may be the product of an animal having transgenic human Ig Constant region genes (see for example WO90/10077 and WO90/04036). Alternatively, the Ab of interest may be genetically engineered to substitute the $CH_1$, $CH_2$, $CH_3$, hinge domains, and/or the framework domain with the corresponding human sequence (see WO92/02190).

Single Chain Antibodies

The Ab of the present invention may be produced as a single chain Ab or scFv instead of the normal multimeric structure. Single chain Abs include the hypervariable regions from an Ig of interest and recreate the antigen binding site of the native Ig while being a fraction of the size of the intact Ig (Skerra, A. et al. (1988) *Science*, 240: 1038-1041; Pluckthun, A. et al. (1989) *Methods Enzymol.* 178: 497-515; Winter, G. et al. (1991) *Nature*, 349: 293-299); Bird et al., (1988) *Science* 242:423; Huston et al. (1988) *Proc. Natl. Acad. Sci. USA* 85:5879; Jost C R et al., *J Biol Chem.* 1994 269:26267-26273; U.S. Pat. Nos. 4,704,692, 4,853,871, 4,94,6778, 5,260,203, 5,455,030). DNA sequences encoding the V regions of the H chain and the L chain are ligated to a linker encoding at least about 4 amino acids (typically small neutral amino acids). The protein encoded by this fusion allows assembly of a functional variable region that retains the specificity and affinity of the original Ab.

One method of producing the Abs of the present invention is to link two or more peptides or polypeptides together by protein chemistry techniques. For example, peptides or polypeptides can be chemically synthesized using currently available laboratory equipment using either Fmoc (9-fluorenylmethyloxycarbonyl) or tBoc (tert-butyloxycarbonyl) chemistry. (Applied Biosystems, Inc., Foster City, Calif.). One skilled in the art can readily appreciate that a peptide or polypeptide corresponding to an Ab chain or antigen-binding fragment thereof can be synthesized by standard chemical reactions. For example, a peptide or polypeptide can be synthesized but not cleaved from its synthesis resin whereas the other fragment of an Ab can be synthesized and subsequently cleaved from the resin, thereby exposing a terminal group which is functionally blocked on the other fragment. By peptide condensation reactions, these two fragments can be covalently joined via a peptide bond at their C- and N-termini, respectively, to form an Ab, or a fragment thereof. (Grunt, G A, *Synthetic Peptides: A User Guide*, W.H. Freeman and Co., N.Y. (1992); Bodansky, M et al., eds, *Principles of peptide Synthesis*, Springer-Verlag Inc., N.Y. (1993))

Antibodies can be selected for particular desired properties. In the case of an Ab to be used in vivo, Ab screening procedures can include any of the in vitro or in vivo bioassays that measure binding to e.g., uPA/uPAR or uPAR-integrin complex, to cells expressing the relevant polypeptide or peptide epitope. Moreover, the Abs may be screened in various of tumor models such as a xenogeneic mouse model in which a human tumor cell line expressing the antigen is grown in immunocompromised, e.g., nude, mice.

Diagnostically Labeled Antibody

The term "diagnostically labeled" means that the present Ab has attached to it a diagnostically detectable label. There are many different labels and methods of labeling known to those of ordinary skill in the art, described below. General classes of labels which can be used in the present invention include radioactive isotopes, paramagnetic isotopes, and compounds which can be imaged by positron emission tomography (PET), fluorescent or colored compounds, etc. Suitable detectable labels include radioactive, fluorescent, fluorogenic, chromogenic, or other chemical labels. Useful radiolabels (radionuclides), which are detected simply by gamma counter, scintillation counter or autoradiography include $^3H$, $^{125}I$, $^{131}I$, $^{35}S$ and $^{14}C$. $^{131}I$ is also a useful therapeutic isotope (see below).

A number of U.S. patents, incorporated by reference herein, disclose methods and compositions for complexing metals to larger molecules, including description of useful chelating agents. The metals are preferably detectable metal atoms, including radionuclides, and are complexed to proteins and other molecules. These documents include: U.S. Pat. Nos. 5,627,286; 5,618,513; 5,567,408; 5,443,816; and 5,561,220.

Common fluorescent labels include fluorescein, rhodamine, dansyl, phycoerythrin, phycocyanin, allophycocyanin, o-phthaldehyde and fluorescamine. The fluorophore, such as the dansyl group, must be excited by light of a particular wavelength to fluoresce. See, for example, Haugland, *Handbook of Fluorescent Probes and Research Chemicals*, Sixth Ed., Molecular Probes, Eugene, Oreg., 1996). Fluorescein, fluorescein derivatives and fluorescein-like molecules such as Oregon Green™ and its derivatives, Rhodamine Green™ and Rhodol Green™, are coupled to amine groups using the isothiocyanate, succinimidyl ester or dichlorotriazinyl-reactive groups. Similarly, fluorophores may also be coupled to thiols using maleimide, iodoacetamide, and aziridine-reactive groups. The long wavelength rhodamines, which are basically Rhodamine Green™ derivatives with substituents on the nitrogens, are among the most photostable fluorescent labeling reagents known. Their spectra are not affected by changes in pH between 4 and 10, an important advantage over the fluoresceins for many biological applications. This group includes the tetramethylrhodamines, X-rhodamines and Texas Red™ derivatives. Other preferred fluorophores for derivatizing the peptide according to this invention are those which are excited by ultraviolet light. Examples include cascade blue, coumarin derivatives, naphthalenes (of which dansyl chloride is a member), pyrenes and pyridyloxazole derivatives. Also included as labels are two related inorganic materials that have recently been described: semiconductor nanocrystals, comprising, for example, cadmium sulfate (Bruchez, M et al., *Science* 281:2013-2016 (1998), and quantum dots, e.g., zinc-sulfide-capped Cd selenide (Chan, W C et al., Science 281:2016-2018 (1998)).

In yet another approach, the amino group of the Ab is allowed to react with reagents that yield fluorescent products, for example, fluorescamine, dialdehydes such as o-phthaldialdehyde, naphthalene-2,3-dicarboxylate and anthracene-2,3-dicarboxylate. 7-nitrobenz-2-oxa-1,3-diazole (NBD) derivatives, both chloride and fluoride, are useful to modify amines to yield fluorescent products.

The Ab of the invention can also be labeled for detection using fluorescence-emitting metals such as $^{152}Eu$, or others of the lanthanide series. These metals can be attached to the peptide using such metal chelating groups as diethylenetriaminepentaacetic acid (DTPA, see Example X, infra) or ethylene-diaminetetraacetic acid (EDTA). DTPA, for example, is available as the anhydride, which can readily modify the $NH_2$-containing peptides of this invention.

For in vivo diagnosis or therapy, radionuclides may be bound to the Ab either directly or indirectly using a chelating agent such as DTPA and DOTA. Examples of such radionuclides are $^{99}Tc$, $^{123}I$, $^{125}I$, $^{131}I$, $^{111}In$, $^{97}Ru$, $^{67}Cu$, $^{67}Ga$, $^{68}Ga$, $^{72}As$, $^{89}Zr$, $^{90}Y$ and $^{201}Tl$. Generally, the amount of labeled Ab needed for detectability in diagnostic use will vary depending on considerations such as age, condition, sex, and extent of disease in the patient, contraindications, if any, and other variables, and is to be adjusted by the individual physician or diagnostician. Dosage can vary from 0.001 mg/kg to 100 mg/kg.

The Ab can also be made detectable by coupling to a phosphorescent or a chemiluminescent compound. The presence of the chemiluminescent-tagged peptide is then determined by detecting the presence of luminescence that arises during the course of a chemical reaction. Examples of particularly useful chemiluminescers are luminol, isoluminol, theromatic acridinium ester, imidazole, acridinium salt and oxalate ester. Likewise, a bioluminescent compound may be used to label the peptides. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and acquorin.

In yet another embodiment, colorimetric detection is used, based on chromogenic compounds which have, or result in, chromophores with high extinction coefficients.

In situ detection of the labeled peptide may be accomplished by removing a histological specimen from a subject and examining it by microscopy under appropriate conditions to detect the label. Those of ordinary skill will readily perceive that any of a wide variety of histological methods (such as staining procedures) can be modified in order to achieve such in situ detection.

For diagnostic in vivo radioimaging, the type of detection instrument available is a major factor in selecting a radionuclide. The radionuclide chosen must have a type of decay which is detectable by a particular instrument. In general, any conventional method for visualizing diagnostic imaging can be utilized in accordance with this invention. Another factor in selecting a radionuclide for in vivo diagnosis is that its half-life be long enough so that the label is still detectable at the time of maximum uptake by the target tissue, but short enough so that deleterious irradiation of the host is minimized. In one preferred embodiment, a radionuclide used for in vivo imaging does not emit particles, but produces a large number of photons in a 140-200 keV range, which may be readily detected by conventional gamma cameras.

In vivo imaging may be used to detect occult metastases which are not observable by other methods. Imaging could be used, for example, to stage tumors non-invasively.

Use of Antibodies to Detect uPA- or uPAR-Complexes by Immunoassay

Antibodies of this invention are useful in immunoassays to detect molecules containing these epitopes in tissue sample or a body fluid, such as serum or plasma. Such Abs would detect the antigen or an epitope-bearing fragment thereof. Thus, if proteolysis in the tumor milieu results in release of the fragments or in tissue.

Any conventional immunoassay known in the art may be employed for this purpose, though Enzyme Immunoassays such as ELISA are preferred. Immunoassay methods are also described in references cited above.

Competitive immunoassays are typically used to detect molecules in a test sample that are ligands for the complex that may mimic the mAbs in their binding specificity, affinity, capacity, etc. In one embodiment a competitive binding assay, the amount of Ab bound to the complex is measured (directly or indirectly using a labeled anti-Ig). Competition (i.e., less binding of Ab to complex) in the presence of the test sample is evidence that one or more components of the sample bind to the complex. It is expected that most compounds being tested will bind with moderate affinities (approximately 1-10 µM).

In another embodiment, a solid support, e.g., a microplate, is coated with the mAb of interest. The test sample is added and incubated, e.g., for about 30 minutes to allow binding of relevant molecules to the Ab. The plates are washed and the complex, in detectably labeled form (e.g., biotinylated), is added as the competitive ligand, and allowed to compete with the test sample for binding to the Ab. A "positive" result for the test sample will be expressed as less binding of labeled complex bound to the solid phase. This approach, in which the complex solution and sample solution are not added simultaneously, avoids the confounding effects of test sample binding directly to the complex, because any test sample present must first be captured by the immobilized mAb. Preferably, to assure that binding is specific, a series of dilutions are run to obtain a dilution curve. This will show if, for example, there is 50% less binding/signal ratio with half the sample. In the absence of such dilution effects, it may be concluded that multiple binding entities are entering into the assay. Results are more rigorous if molecules binding at the mAb binding site have similar affinities.

Immunohistochemical Assays

One preferred assay for detecting the antigens in a tissue is by immunohistochemistry, using any conventional assay methods, with which the art is replete. A preferred assay is the one described in the Examples below. For a description of such methods, see, for example, Dabbs, D J, *Diagnostic Immunohistochemistry*, Churchill Livingstone, 2001, which is incorporated by reference in its entirety.

Non-Histological Immunoassays

Preferred immunoassays are enzyme immunoassays (EIA's) such as ELISA, which employ antigens or Abs immobilized to solid supports. For the present compositions and methods, the solid support is preferably any one of polystyrene, polypropylene, polyethylene, dextran, nylon, polyacrylamide, polyvinylidene difluoride, natural cellulose, modified cellulose, nitrocellulose, agarose and magnetic beads. In a preferred embodiment, the surface of polystyrene or other plastic multiwell plates serves as the solid support. In another embodiment, a solid support to which the Ab or antigen is affixed to the bottom or placed loosely in the wells of multiwell plates. Multiwell plates in which the bottoms of the wells comprise nitrocellulose or a similar membrane material and through which liquid can be moved under pressure or vacuum may also be used.

Typical, and preferred, immunoassays include "forward" assays in which the Ab immobilized to a solid support is first contacted with the sample being tested to bind or "extract" the antigen from the sample by formation of a binary immobilized Ab-antigen complex. After suitable incubation, the solid support is washed to remove the residue of the fluid sample including unbound antigen, if any, and then contacted with the solution containing an unknown quantity of labeled Ab (which functions as a "reporter molecule"). After a second incubation, that permits the labeled Ab to complex with the immobilized antigen through the unlabeled Ab, the solid support is washed a second time to remove the unreacted labeled Ab and the immobilized label is measured. This type of forward sandwich assay may be a simple "yes/no" assay to determine whether antigen is present or may be made quantitative by comparing the amount of immobilized labeled Ab with the amount immobilized when a standard sample containing a known quantity of antigen is used.

So called "simultaneous" and "reverse" sandwich assays may also be used. A simultaneous assay involves a single incubation step as the immobilized Ab and labeled Ab are added simultaneously to the sample. After appropriate incubation, the solid support is washed to remove residue of the sample and uncomplexed labeled Ab. The presence or amount of labeled Ab associated with the solid support is then determined as in the above conventional "forward" sandwich assay.

In a "reverse" assay, a solution of labeled Ab is added to the sample after a suitable incubation period followed by addition of immobilized unlabeled Ab. After a second incubation, the solid phase material is washed in conventional fashion to free it of the residue of the sample and unreacted labeled Ab. The determination of immobilized Ab associated with the solid support is then determined as in the "simultaneous" and "forward" assays.

Assay for Antibody Binding to uPAR on Whole Cells

The uPAR-targeting Ab and/or conjugate thereof is readily tested for binding to uPAR, preferably by measuring inhibition of the binding of [$^{125}$I]DFP-uPA to uPAR in a competitive ligand-binding assay or by directly labeling the Ab with [$^{125}$I]. The assay may employ whole cells that express uPAR, for example cells lines such as A2780 or HeLa. A preferred assay is conducted as follows. Cells (about $5 \times 10^4$/well) are plated in medium (e.g., MEM with Earle's salts/10% FBS+ antibiotics) in 24-well plates, then incubated in a humid 5% $CO_2$ atmosphere until the cells reach 70% confluence. Catalytically inactivated high molecular weight uPA (DFP-uPA) is radioiodinated using Iodo-gen® (Pierce) to a specific activity of about 250,000 cpm/µg. The cell-containing plates are then chilled on ice and the cells are washed twice (5 minutes each) with cold PBS/0.05% Tween-80. Test Abs and/or conjugates thereof are serially diluted in cold PBS/0.1% BSA/ 0.01% Tween-80 and added to each well to a final volume of 0.3 mL 10 minutes prior to the addition of the [$^{125}$I]DFP-uPA. Each well then receives 9500 cpm of [$^{125}$I]DFP-uPA at a final concentration of 0.2 nM). The plates are then incubated at 4° C. for 2 hrs, after which time the cells are washed 3× (5 minutes each) with cold PBS/0.05% Tween-80. NaOH (1N) is added to each well in 0.5 mL to lyse the cells, and the plate is incubated for 5 minutes at room temperature or until all the cells in each well are lysed as determined by microscopic examination. The contents of each well are then aspirated and the total counts in each well determined using a gamma counter. Each compound is tested in triplicate and the results are expressed as a percentage of the total radioactivity measured in wells containing [$^{125}$I]DFP-uPA alone, which is taken to represent maximum (100%) binding.

The inhibition of binding of [$^{125}$I]DFP-uPA to uPAR is usually dose-related, such that the concentration of the test compound necessary to produce a 50% inhibition of binding (the $IC_{50}$ value), which is expected to fall in the linear part of the curve, is easily determined. In general, Abs and/or conjugates thereof have $IC_{50}$ values of less than about $10^{-5}$ M. Preferably, Abs and/or conjugates thereof have $IC_{50}$ values of less than about $10^{-6}$ M, more preferably, less than about $10^{-7}$ M.

Assays of Biological Activity of Anti-uPAR Antibodies or Other Ligands

Those of skill in the art will appreciate that the in vitro and in vivo assays useful for measuring the activity of the Abs or other uPAR-binding ligands of the invention or of conjugates thereof, as described herein, are intended to be illustrative and neither comprehensive nor limiting.

Assay for EC Migration

For EC migration studies, transwells are coated with type I collagen (50 µg/nl) by adding 200 µL of the collagen solution per transwell, then incubating overnight at 37° C. The transwells are assembled in a 24-well plate and a chemoattractant (e.g., FGF-2) is added to the bottom chamber in a total volume of 0.8 mL media. ECs, such as human umbilical vein endothelial cells (HUVEC), which have been detached from monolayer culture using trypsin, are diluted to a final concentration of about $10^6$ cells/mL with serum-free media and 0.2 mL of this cell suspension is added to the upper chamber of each transwell. Inhibitors to be tested may be added to both the upper and lower chambers and the migration is allowed to proceed for 5 hrs in a humidified atmosphere at 37° C. The transwells are removed from the plate stained using DiffQuik®. Cells which did not migrate are removed from the upper chamber by scraping with a cotton swab and the membranes are detached, mounted on slides, and counted under a high-power field (400×) to determine the number of cells migrated.

Biological Assay of Anti-Invasive Activity

The ability of cells such as ECs or tumor cells (e.g., PC-3 human prostatic carcinoma cells) to invade through a reconstituted basement membrane (Matrigel®) in an assay known as a Matrigel® invasion assay system is well known (Kleinman et al., *Biochemistry* 1986, 25: 312-318; Parish et al., 1992, *Int. J. Cancer* 52:378-383). Matrigel® is a reconstituted basement membrane containing type IV collagen, laminin, heparan sulfate proteoglycans such as perlecan (which bind to and localize bFGF), vitronectin as well as transforming growth factor-β (TGFβ), urokinase-type plasminogen activator (uPA), tissue plasminogen activator (tPA) and the serpin known as plasminogen activator inhibitor type 1 (PAI-1) (Chambers et al., *Canc. Res.* 1995, 55:1578-1585). It is accepted in the art that results obtained in this type of assay for Abs and/or conjugates thereof or other ligands which target extracellular receptors or enzymes are predictive of the efficacy of these Abs and/or conjugates thereof in vivo (Rabbani et al., *Int. J. Cancer* 1995, 63: 840-845).

Such assays employ transwell tissue culture inserts. Invasive cells are defined as cells which traverse through the Matrigel® and upper aspect of a polycarbonate membrane and adhere to the bottom of the membrane. Transwells (e.g., from Costar) containing polycarbonate membranes (8.0 μm pore size) are coated with Matrigel® (e.g., from Collaborative Research), which has been diluted in sterile PBS to a final concentration of about 75 μg/mL (e.g., 60 μL of diluted Matrigel® per insert), and placed in the wells of a 24-well plate. The membranes are dried overnight in a biological safety cabinet, then rehydrated by adding 100 μL of medium, e.g., DMEM, supplemented with antibiotics for 1 hour on a shaker table. The DMEM is removed from each insert by aspiration and 0.8 mL of complete DMEM (+/10% FBS and antibiotics) is added to each well of the 24-well plate such that it surrounds the outside of the transwell ("lower chamber"). Fresh DMEM with antibiotics (100 μL), human Glu-plasminogen (5 μg/mL), and any inhibitors to be tested are added to the top, inside of the transwell ("upper chamber"). The cells which are to be tested are trypsinized and resuspended in DMEM+ antibiotics and added to the top chamber of the transwell at a final concentration of about $8 \times 10^5$ cells/mL. The final volume of the upper chamber is adjusted to 200 μL. The assembled plate is then incubated in a humid 5% $CO_2$ atmosphere for about 72 hours. After incubation, the cells are fixed and stained using DiffQuik® (Giemsa stain) and the upper chamber is then scraped using a cotton swab to remove the Matrigel® and any cells which did not invade through the membrane. The membranes are detached from the transwell using an X-acto® blade, mounted on slides using Permount® and coverslips, then counted under a microscope using high power (e.g., 400×). A mean number of invading cells from 5-10 counted fields is calculated and plotted as a function of inhibitor concentration.

Tube-Formation Assays of Anti-Angiogenic Activity

ECs, for example, human umbilical vein endothelial cells (HUVEC) or human microvascular endothelial cells (HMVEC) which can be prepared or obtained commercially, are mixed at a concentration of $2 \times 10^5$ cells/mL with fibrinogen (5 mg/mL in phosphate buffered saline (PBS) in a 1:1 (v/v) ratio. Thrombin is added (5 units/mL final concentration) and the mixture is immediately transferred to a 24-well plate (0.5 mL per well). The fibrin gel is allowed to form and then VEGF and bFGF are added to the wells (each at 5 mg/mL final concentration) along with the test compound. The cells are incubated at 37° C. in 5% $CO_2$ for 4 days at which time the cells in each well are counted and classified as either rounded, elongated with no branches, elongated with one branch, or elongated with 2 or more branches. Results are expressed as the average of 5 different wells for each concentration of compound. Typically, in the presence of angiogenic inhibitors, cells remain either rounded or form undifferentiated tubes (e.g. 0 or 1 branch). This assay is recognized in the art to be predictive of angiogenic (or anti-angiogenic) efficacy in vivo (Min et al., *Cancer Res.* 1996, 56: 2428-2433).

In an alternate assay, EC tube formation is observed when ECs are cultured on Matrigel® (Schnaper H W et al., *J. Cell. Physiol.* 1995, 165:107-118). $10^4$ EC/well are transferred onto Matrigel®-coated 24-well plates, and tube formation is quantitated after 48 hrs. Inhibitors are tested by adding them either at the time of adding the ECs or at various time points thereafter. Tube formation can also be stimulated by adding (a) an angiogenic growth factor such as bFGF or VEGF, (b) a differentiation stimulating agent (e.g., PMA) or (c) a combination of these.

While not wishing to be bound by theory, this assay models angiogenesis by presenting to the ECs a particular type of basement membrane, namely the layer of matrix which migrating and differentiating ECs would be expected to encounter first. In addition to bound growth factors, the matrix components found in Matrigel® (and in basement membranes in situ), or proteolytic products thereof, may also be stimulatory for EC tube formation which makes this model complementary to the fibrin gel angiogenesis model previously described (Blood, C H et al., *Biochim. Biophys. Acta* 1990, 1032:89-118; Odedra, R et al., *Pharmac. Ther.* 1991, 49:111-124).

Assays for Inhibition of Cell Proliferation

The ability of the Abs and/or conjugates of this invention to inhibit the proliferation of ECs may be determined in a 96-well format. Type I collagen (gelatin) is used to coat the wells of the plate (0.1-1 mg/mL in PBS, 0.1 mL per well for 30 minutes at room temperature). After washing the plate (3× using PBS), $3-6 \times 10^3$ cells are plated per well and allowed to attach for 4 hrs (37° C./5% $CO_2$) in Endothelial Growth Medium (EGM; Clonetics) or M199 medium supplemented with 0.1-2% FBS. The medium and any unattached cells are removed at the end of 4 hrs and fresh medium supplemented with bFGF (1-10 ng/mL) or VEGF (1-10 ng/mL) is added to each well. Antibodies and/or conjugates to be tested are added last, and the plate is allowed to incubate (37° C./5% $CO_2$) for 24-48 hrs. The chromogenic compound MTS (Promega) is added to each well and allowed to incubate from 1-4 hrs. The color developing in each well is directly proportional to the cell number, thereby serving as a surrogate for counting cells. Absorbance read at 490 nm is used to determine the differences in cell numbers, i.e., proliferation, between control wells and those containing test Abs and/or conjugates.

A similar assay employing cultured adherent tumor cells may also be used. However, collagen may be omitted in this format. Tumor cells (e.g., 3-10×10³/well) are plated and allowed to adhere overnight. Serum-free medium is then added, and the cells forced to synchronize for 24 hrs. Medium+10% FBS is then added to each well to stimulate proliferation. Antibodies and/or conjugates to be tested are included in some of the wells. After 24 hrs, MTS is added to the plate and the assay developed and read as above.

Assays of Cytotoxicity

The anti-proliferative and cytotoxic effects of Abs and/or conjugates thereof may be determined for various cell types including tumor cells, ECs, fibroblasts and macrophages. This is especially useful when testing a Ab which has been conjugated to a therapeutic moiety such as a radiotherapeutic or a toxin. For example, a conjugate of one of the Abs of the invention with Bolton-Hunter reagent which has been iodinated with $^{131}$I would be expected to inhibit the proliferation of cells expressing uPAR (most likely by inducing apoptosis). Anti-proliferative effects would be expected against tumor cells and stimulated endothelial cells but, under some circumstances not quiescent endothelial cells or normal human dermal fibroblasts. Any anti-proliferative or cytotoxic effects observed in the normal cells may represent non-specific toxicity of the conjugate.

A typical assay would involve plating cells at a density of 5-10,000 cells per well in a 96-well plate. The compound to be tested is added at a concentration 10× the $IC_{50}$ measured in a binding assay (this will vary depending on the conjugate) and allowed to incubate with the cells for 30 minutes. The cells are washed 3× with media, then fresh media containing [$^3$H]thymidine (1 μCi/mL) is added to the cells and they are allowed to incubate at 37° C. in 5% $CO_2$ for 24 and 48 hours. Cells are lysed at the various time points using 1 M NaOH and counts per well determined using a β-counter. Proliferation may be measured non-radioactively using MTS reagent or CyQuant® to measure total cell number. For cytotoxicity assays (measuring cell lysis), a Promega 96-well cytotoxicity kit is used. If there is evidence of anti-proliferative activity, induction of apoptosis may be measured using TumorTACS (Genzyme).

Assay of Caspase-3 Activity

The ability of the Abs and/or conjugates to promote apoptosis of EC's may be determined by measuring activation of caspase-3. Type I collagen (gelatin) is used to coat a P100 plate and 5×10⁵ ECs are seeded in EGM+10% FBS. After 24 hours (at 37° C./5% $CO_2$) the medium is replaced by EGM+2% FBS, 10 ng/ml bFGF and the desired test compound. The cells are harvested after 6 hrs, cell lysates prepared in 1% Triton X-100 detergent, and the lysates assayed using the EnzChek®Caspase-3 Assay Kit #1 (Molecular Probes) according to the manufactures' instructions.

Corneal Angiogenesis Model

The protocol used is essentially identical to that described by Volpert, O V et al., *J. Clin. Invest.* 1996, 98:671-679. Briefly, female Fischer rats (120-140 gms) are anesthetized and pellets (5 μl) comprised of Hydron®, bFGF (150 nM), and the Abs and/or conjugates thereof to be tested are implanted into tiny incisions made in the cornea 1.0-1.5 mm from the limbus. Neovascularization is assessed at 5 and 7 days after implantation. On day 7, animals are anesthetized and infused with a dye such as colloidal carbon to stain the vessels. The animals are then euthanized, the corneas fixed with formalin, and the corneas flattened and photographed to assess the degree of neovascularization. Neovessels may be quantitated by imaging the total vessel area or length or simply by counting vessels.

Chick Chorioallantoic Membrane (CAM) Angiogenesis Assay

This assay is performed essentially as described by Nguyen et al., *Microvascular Res.* 1994, 47:3140. A mesh containing either angiogenic factors (bFGF) or tumor cells plus a test compound, here the anti-uPAR Abs or conjugates, placed onto the CAM of an 8-day old chick embryo and the CAM observed for 3-9 days after implantation of the sample. Angiogenesis is quantitated by determining the percentage of squares in the mesh which contain visible blood vessels.

Matrigel® Plug Assay

This assay is performed essentially as described by Passaniti, A et al., 1992, *Lab Invest.* 67:519-528. Ice-cold Matrigel® (e.g., 500 μL) (Collaborative Biomedical Products, Inc., Bedford, Mass.) is mixed with heparin (e.g., 50 ng/ml), FGF-2 (e.g., 400 ng/ml) and the compound to be tested. In some assays, bFGF may be substituted with tumor cells as the angiogenic stimulus. The Matrigel® mixture is injected subcutaneously (s.c.) into 4-8 week-old athymic nude mice at sites near the abdominal midline, preferably 3 injections per mouse. The injected Matrigel® forms a palpable solid gel. Injection sites are chosen such that each animal receives a positive control plug (such as FGF2+heparin), a negative control plug (e.g., buffer+heparin) and a plug that includes the compound being tested for its effect on angiogenesis, e.g., (FGF-2+heparin+compound). All treatments groups are preferably run in triplicate. Animals are sacrificed by cervical dislocation at about 7 days post injection or another time that may be optimal for observing angiogenesis. The mouse skin is detached along the abdominal midline, and the Matrigel® plugs are recovered and scanned microscopically immediately at high resolution. Plugs are then dispersed in water and incubated at 37° C. overnight. Hemoglobin (Hb) levels in the plugs are determined using Drabkin's solution (e.g., from Sigma) according to the manufacturers' instructions. The amount of Hb in the plug is an indirect measure of angiogenesis as it reflects the amount of blood in the sample.

In addition, or alternatively, animals may be injected prior to sacrifice with a 0.1 ml buffer (preferably PBS) containing a high molecular weight dextran to which is conjugated a fluorophore. The amount of fluorescence in the dispersed plug, determined fluorimetrically, also serves as a measure of angiogenesis in the plug. Staining with mAb anti-CD31 (CD31 is "platelet-endothelial cell adhesion molecule", "PECAM") may also be used to confirm neovessel formation and microvessel density in the plugs.

In Vivo Assessment of Angiogenesis Inhibition and Anti-Tumor Effects Using the Matrigel® Plug Assay with Tumor Cells In this assay, tumor cells, for example 1-5×10⁶ cells of the 3LL Lewis lung carcinoma or the rat prostate cell line Mat-LyLu, are mixed with Matrigel® and then injected into the flank of a mouse following the protocol described above. A mass of tumor cells and a powerful angiogenic response can be observed in the plugs after about 5 to 7 days. The anti-tumor and anti-angiogenic action of a compound in an actual tumor environment can be evaluated by including it in the plug. Measurement is then made of tumor weight, Hb levels or fluorescence levels (of a dextran-fluorophore conjugate injected prior to sacrifice). To measure Hb or fluorescence, the plugs are first homogenized with a tissue homogenizer.

Xenograft Models of Subcutaneous Tumor Growth

Human Ovarian Carcinoma

A2780 human ovarian cancer line was established from tumor tissue from an untreated patient. The A2780 cells are maintained as a monolayer in RPMI 1640 medium supplemented with 2 mM glutamine, 0.01 mg/mL bovine insulin, and 10% FBS. (Hamilton, T C et al., *Sem. Oncol.* 1984; 11:285-293; Behrens, B C et al., *Cancer Res.* 1987; 47:414-418). Two million A2780 are inoculated in the right flank of nude Balb/c female mice. The A2780 tumor is staged to 50 to 200 mm$^3$ range before treatment is. The IgG control Ab as well as the anti-D2D3 uPAR mAbs are administered by the intraperitoneal route at 10 mg/kg twice weekly on Monday and Friday. The cisplatin treatment group was staged to 1000 mm$^3$; animals received 6 mg/kg once a week. Tumor volumes were measured twice a week. At the time of sacrifice, plasma is obtained and the tumor excised from each animal. Half of the tumor is snap frozen for biochemical assessment and the rest is placed in Zinc fixative for histological assessment.

Human Lung Carcinoma

A549, human lung carcinoma (ATCC Catalog No. CCL-185) cell line, was established through explant culture of lung carcinomatous tissue from a 58-year-old Caucasian male (Giard, D J et al., *J. Natl. Cancer Inst.* 51:1417-23 (1973)). A549 cells are maintained in Ham's F12K medium supplemented with 2 mM L-glutamine, 0.15% NaHCO$_3$, and 10% FBS.

About 10$^6$ A549 carcinoma cells are inoculated in the right flank of C.B-17/Sys (scid/scid) Severe Combined Immunodeficient (SCID) female mice. Treatment is preferably initiated the day after tumor inoculation. The IgG control Ab (and the PBS control) as well as the anti-D2D3 uPAR mAb ATN-658 are administered intraperitoneally 10 mg/kg twice weekly on Monday and Friday. Initially tumor volumes are measured once a week. When the volume in any treatment group exceeds 300 mm$^3$, measurements are obtained twice a week.

At the time of sacrifice, plasma is obtained and the tumor excised from each animal. Half of the tumor is snap frozen for biochemical assessment and the rest is placed in Zinc fixative for histological assessment.

Xenograft Model of Metastasis

The Abs and/or conjugates are tested for inhibition of late metastasis using an experimental metastasis model such as that of Crowley et al., *Proc. Natl. Acad. Sci. USA* 1993, 90 5021-5025). Late metastasis involves the steps wherein tumor cells attach and extravasate, invade locally, seed, proliferate and induce angiogenesis. Human prostatic carcinoma cells (PC-3) transfected with a reporter gene, preferably the green fluorescent protein (GFP) gene, but as an alternative with a gene encoding the enzymes chloramphenicol acetyl-transferase (CAT), luciferase or LacZ, are inoculated into nude mice. This approach permits utilization of either of these markers (fluorescence detection of GFP or histochemical calorimetric detection of the various enzymes) to follow the fate of these cells. Cells are injected, preferably iv, and metastases identified after about 14 days, particularly in the lungs but also in regional lymph nodes, femurs and brain. This mimics the organ tropism of naturally occurring metastases in human prostate cancer. For example, GFP-expressing PC-3 cells (10$^6$ cells per mouse) are injected iv into the tail veins of nude (nu/nu) mice. Animals are treated with a test composition at 100 μg/animal/day given q.d. IP. Single metastatic cells and foci are visualized and quantitated by fluorescence microscopy or light microscopic histochemistry or by grinding the tissue and quantitative calorimetric assay of the detectable label.

Pharmaceutical and Therapeutic Compositions and their Administration

The compounds that may be employed in the pharmaceutical compositions of the invention include all of the polypeptide molecules, preferably Abs, described above, as well as the pharmaceutically acceptable salts of these compounds. Pharmaceutically acceptable acid addition salts of the compounds of the invention containing a basic group are formed where appropriate with strong or moderately strong, non-toxic, organic or inorganic acids by methods known to the art. Exemplary of the acid addition salts that are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts.

Pharmaceutically acceptable base addition salts of compounds of the invention containing an acidic group are prepared by known methods from organic and inorganic bases and include, for example, nontoxic alkali metal and alkaline earth bases, such as calcium, sodium, potassium and ammonium hydroxide; and nontoxic organic bases such as triethylamine, butylamine, piperazine, and tri(hydroxymethyl)methylamine.

As stated above, the compounds of the invention possess the ability to inhibit EC proliferation, motility, or invasiveness and angiogenesis, properties that are exploited in the treatment of cancer, in particular metastatic cancer. A composition of this invention may be active per se, or may act as a "pro-drug" that is converted in vivo to the active form.

Therapeutically Labeled Compositions

In a preferred embodiment, the mAbs describe herein are "therapeutically conjugated" or "therapeutically labeled" (terms which are intended to be interchangeable) and used to deliver a therapeutic agent to the site to which the compounds home and bind, such as sites of tumor metastasis or foci of infection/inflammation, restenosis or fibrosis. The term "therapeutically conjugated" means that the modified mAb is conjugated to another therapeutic agent that is directed either to the underlying cause or to a "component" of tumor invasion, angiogenesis, inflammation or other pathology. A therapeutically labeled polypeptide carries a suitable therapeutic "label" also referred to herein as a "therapeutic moiety." A therapeutic moiety is an atom, a molecule, a compound or any chemical component added to the peptide that renders it active in treating a target disease or condition, primarily one a associated with undesired angiogenesis. The therapeutic moiety may be bound directly or indirectly to the mAb. The therapeutically labeled mAb is administered as pharmaceutical composition which comprises a pharmaceutically acceptable carrier or excipient, and is preferably in a form suitable for injection.

Examples of useful therapeutic radioisotopes (ordered by atomic number) include $^{47}$Sc, $^{67}$Cu, $^{90}$Y, $^{109}$Pd, $^{125}$I, $^{131}$I, $^{186}$Re, $^{188}$Re, $^{199}$Au, $^{211}$At, $^{212}$Pb and $^{217}$Bi. These atoms can be conjugated to the peptide directly, indirectly as part of a chelate, or, in the case of iodine, indirectly as part of an iodinated Bolton-Hunter group. The radioiodine can be introduced either before or after this group is coupled to the peptide compound.

Preferred doses of the radionuclide conjugates are a function of the specific radioactivity to be delivered to the target site which varies with tumor type, tumor location and vascularization, kinetics and biodistribution of the peptide carrier, energy of radioactive emission by the nuclide, etc. Those skilled in the art of radiotherapy can readily adjust the dose of the peptide in conjunction with the dose of the particular nuclide to effect the desired therapeutic benefit without undue experimentation.

Another therapeutic approach included here is the use of boron neutron capture therapy, where a boronated peptide is delivered to a desired target site, such as a tumor, most preferably an intracranial tumor (Barth, R F, *Cancer Invest.* 14:534-550 (1996); Mishima, Y (ed.), *Cancer Neutron Cap-*

*ture Therapy*, New York: Plenum Publishing Corp., 1996; Soloway, A H et al., (eds), *J. Neuro-Oncol.* 33.1-188 (1997). The stable isotope $^{10}$B is irradiated with low energy (<0.025 eV) thermal neutrons, and the resulting nuclear capture yields α-particles and $^7$Li nuclei which have high linear energy transfer and respective path lengths of about 9 and 5 μm. This method is predicated on $^{10}$B accumulation in the tumor with lower levels in blood, endothelial cells and normal tissue (e.g., brain). Such delivery has been accomplished using epidermal growth factor (Yang. W et al., *Cancer Res* 57:4333-4339 (1997).

Other therapeutic agents which can be coupled to the mAbs according to the method of the invention are drugs, prodrugs, enzymes for activating pro-drugs, photosensitizing agents, nucleic acid therapeutics, antisense vectors, viral vectors, lectins and other toxins.

Lectins are proteins, commonly derived from plants, that bind to carbohydrates. Among other activities, some lectins are toxic. Some of the most cytotoxic substances known are protein toxins of bacterial and plant origin (Frankel, A E et al., *Ann. Rev. Med.* 37:125-142 (1986)). These molecules binding the cell surface and inhibit cellular protein synthesis. The most commonly used plant toxins are ricin and abrin; the most commonly used bacterial toxins are diphtheria toxin and *Pseudomonas* exotoxin A. In ricin and abrin, the binding and toxic functions are contained in two separate protein subunits, the A and B chains. The ricin B chain binds to the cell surface carbohydrates and promotes the uptake of the A chain into the cell. Once inside the cell, the ricin A chain inhibits protein synthesis by inactivating the 60S subunit of the eukaryotic ribosome Endo, Y. et al., *J. Biol. Chem.* 262: 5908-5912 (1987)). Other plant derived toxins, which are single chain ribosomal inhibitory proteins, include pokeweed antiviral protein, wheat germ protein, gelonin, dianthins, momorcharins, trichosanthin, and many others (Strip, F. et al., *FEBS Lett.* 195:1-8 (1986)). Diphtheria toxin and *Pseudomonas* exotoxin A are also single chain proteins, and their binding and toxicity functions reside in separate domains of the same protein *Pseudomonas* exotoxin A has the same catalytic activity as diphtheria toxin. Ricin has been used therapeutically by binding its toxic α-chain, to targeting molecules such as Abs to enable site-specific delivery of the toxic effect. Bacterial toxins have also been used as anti-tumor conjugates. As intended herein, a toxic peptide chain or domain is conjugated to a compound of this invention and delivered in a site-specific manner to a target site where the toxic activity is desired, such as a metastatic focus. Conjugation of toxins to protein such as Abs or other ligands are known in the art (Olsnes, S. et al., *Immunol. Today* 10:291-295 (1989); Vitetta, E S et al., *Ann. Rev. Immunol.* 3:197-212 (1985)).

Cytotoxic drugs that interfere with critical cellular processes including DNA, RNA, and protein synthesis, have been conjugated to Abs and subsequently used for in vivo therapy. Such drugs, including, but not limited to, daunorubicin, doxorubicin, methotrexate, and Mitomycin C are also coupled to the compounds of this invention and used therapeutically in this form.

The compounds of the invention, as well as the pharmaceutically acceptable salts thereof, may be incorporated into convenient dosage forms, such as capsules, impregnated wafers, tablets or injectable preparations. Solid or liquid pharmaceutically acceptable carriers may be employed.

Solid carriers include starch, lactose, calcium sulfate dihydrate, terra alba, sucrose, talc, gelatin, agar, pectin, acacia, magnesium stearate and stearic acid. Liquid carriers include syrup, peanut oil, olive oil, saline, water, dextrose, glycerol and the like. Similarly, the carrier or diluent may include any prolonged release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g., a solution), such as an ampoule, or an aqueous or nonaqueous liquid suspension. A summary of such pharmaceutical compositions may be found, for example, in *Remington's Pharmaceutical Sciences*, Mack Publishing Company, Easton Pa. (Gennaro 18th ed. 1990).

The pharmaceutical preparations are made following conventional techniques of pharmaceutical chemistry involving such steps as mixing, granulating and compressing, when necessary for tablet forms, or mixing, filling and dissolving the ingredients, as appropriate, to give the desired products for oral, parenteral, topical, transdermal, intravaginal, intrapenile, intranasal, intrabronchial, intracranial, intraocular, intraaural and rectal administration. The pharmaceutical compositions may also contain minor amounts of nontoxic auxiliary substances such as wetting or emulsifying agents, pH buffering agents and so forth.

The present invention may be used in the diagnosis or treatment of any of a number of animal genera and species, and are equally applicable in the practice of human or veterinary medicine. Thus, the pharmaceutical compositions can be used to treat domestic and commercial animals, including birds and more preferably mammals, as well as humans.

The term "systemic administration" refers to administration of a composition or agent such as the polypeptide, described herein, in a manner that results in the introduction of the composition into the subject's circulatory system or otherwise permits its spread throughout the body, such as intravenous (i.v.) injection or infusion. "Regional" administration refers to administration into a specific, and somewhat more limited, anatomical space, such as intraperitoneal, intrathecal, subdural, or to a specific organ. Examples include intravaginal, intrapenile, intranasal, intrabronchial (or lung instillation), intracranial, intra-aural or intraocular. The term "local administration" refers to administration of a composition or drug into a limited, or circumscribed, anatomic space, such as intratumoral injection into a tumor mass, subcutaneous (s.c.) injections, intramuscular (i.m.) injections. One of skill in the art would understand that local administration or regional administration often also result in entry of a composition into the circulatory system, i.e., so that s.c. or i.m. are also routes for systemic administration. Injectables or infusible preparations can be prepared in conventional forms, either as solutions or suspensions, solid forms suitable for solution or suspension in liquid prior to injection or infusion, or as emulsions. Though the preferred routes of administration are systemic, such as i.v., the pharmaceutical composition may be administered topically or transdermally, e.g., as an ointment, cream or gel; orally; rectally; e.g., as a suppository.

For topical application, the compound may be incorporated into topically applied vehicles such as a salve or ointment. The carrier for the active ingredient may be either in sprayable or nonsprayable form. Non-sprayable forms can be semi-solid or solid forms comprising a carrier indigenous to topical application and having a dynamic viscosity preferably greater than that of water. Suitable formulations include, but are not limited to, solution, suspensions, emulsions, creams, ointments, powders, liniments, salves, and the like. If desired, these may be sterilized or mixed with auxiliary agents, e.g., preservatives, stabilizers, wetting agents, buffers, or salts for influencing osmotic pressure and the like. Preferred vehicles for non-sprayable topical preparations include ointment bases, e.g., polyethylene glycol-1000 (PEG-1000); conventional creams such as HEB cream; gels; as well as petroleum jelly and the like.

Also suitable for topic application as well as for lung instillation are sprayable aerosol preparations wherein the compound, preferably in combination with a solid or liquid inert carrier material, is packaged in a squeeze bottle or in admixture with a pressurized volatile, normally gaseous propellant. The aerosol preparations can contain solvents, buffers, surfactants, perfumes, and/or antioxidants in addition to the compounds of the invention.

For the preferred topical applications, especially for humans, it is preferred to administer an effective amount of the compound to an affected area, e.g., skin surface, mucous membrane, eyes, etc. This amount will generally range from about 0.001 mg to about 1 g per application, depending upon the area to be treated, the severity of the symptoms, and the nature of the topical vehicle employed.

Other pharmaceutically acceptable carriers for polypeptide compositions of the present invention are liposomes, pharmaceutical compositions in which the active protein is contained either dispersed or variously present in corpuscles consisting of aqueous concentric layers adherent to lipidic layers. The active polypeptide is preferably present in the aqueous layer and in the lipidic layer, inside or outside, or, in any event, in the non-homogeneous system generally known as a liposomic suspension. The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature. Those skilled in the art will appreciate other suitable embodiments of the present liposomal formulations.

Therapeutic compositions for treating tumors and cancer may comprise, in addition to the peptide, one or more additional anti-tumor agents, such as mitotic inhibitors, e.g., vinblastine; alkylating agents, e.g., cyclophosphamide; folate inhibitors, e.g., methotrexate, piritrexim or trimetrexate; antimetabolites, e.g., 5-fluorouracil and cytosine arabinoside; intercalating antibiotics, e.g., adriamycin and bleomycin; enzymes or enzyme inhibitors, e.g., asparaginase, topoisomerase inhibitors such as etoposide; or biological response modifiers, e.g., interferons or interleukins. In fact, pharmaceutical compositions comprising any known cancer therapeutic in combination with the peptides disclosed herein are within the scope of this invention. The pharmaceutical composition may also comprise one or more other medicaments to treat additional symptoms for which the target patients are at risk, for example, anti-infectives including antibacterial, anti-fungal, anti-parasitic, anti-viral, and anti-coccidial agents.

The therapeutic dosage administered is an amount which is therapeutically effective, as is known to or readily ascertainable by those skilled in the art. The dose is also dependent upon the age, health, and weight of the recipient, kind of concurrent treatment(s), if any, the frequency of treatment, and the nature of the effect desired, such as, for example, anti-inflammatory effects or anti-bacterial effect.

Therapeutic Methods

The methods of this invention may be used to inhibit tumor growth and invasion in a subject or to suppress angiogenesis induced by tumors by inhibiting endothelial cell growth and migration. By inhibiting the growth or invasion of a tumor or angiogenesis, the methods result in inhibition of tumor metastasis. A vertebrate subject, preferably a mammal, more preferably a human, is administered an amount of the compound effective to inhibit tumor growth, invasion or angiogenesis. The compound or pharmaceutically acceptable salt thereof is preferably administered in the form of a pharmaceutical composition as described above.

Doses of the proteins (including Abs), peptides, peptide multimers, etc., preferably include pharmaceutical dosage units comprising an effective amount of the peptide. Dosage unit form refers to physically discrete units suited as unitary dosages for a mammalian subject; each unit contains a predetermined quantity of active material calculated to produce the desired therapeutic effect, in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active compound for the treatment of, and sensitivity of, individual subjects By an effective amount is meant an amount sufficient to achieve a steady state concentration in vivo which results in a measurable reduction in any relevant parameter of disease and may include growth of primary or metastatic tumor, any accepted index of inflammatory reactivity, or a measurable prolongation of disease-free interval or of survival. For example, a reduction in tumor growth in 20% of patients is considered efficacious (Frei III, E., *The Cancer Journal* 3:127-136 (1997)). However, an effect of this magnitude is not considered to be a minimal requirement for the dose to be effective in accordance with this invention.

In one embodiment, an effective dose is preferably 10-fold and more preferably 100-fold higher than the 50% effective dose ($ED_{50}$) of the compound in an in vivo assay as described herein.

The amount of active compound to be administered depends on the precise peptide or derivative selected, the disease or condition, the route of administration, the health and weight of the recipient, the existence of other concurrent treatment, if any, the frequency of treatment, the nature of the effect desired, for example, inhibition of tumor metastasis, and the judgment of the skilled practitioner.

A preferred dose for treating a subject, preferably mammalian, more preferably human, with a tumor is an amount of up to about 100 milligrams of active polypeptide-based compound per kilogram of body weight. A typical single dosage of the peptide or peptidomimetic is between about 1 ng and about 100 mg/kg body weight. For topical administration, dosages in the range of about 0.01-20% concentration (by weight) of the compound, preferably 1-5%, are suggested. A total daily dosage in the range of about 0.1 milligrams to about 7 grams is preferred for intravenous administration. The foregoing ranges are, however, suggestive, as the number of variables in an individual treatment regime is large, and considerable excursions from these preferred values are expected.

An effective amount or dose of the peptide for inhibiting endothelial cell proliferation or migration in vitro is in the range of about 1 picogram to about 5 nanograms per cell. Effective doses and optimal dose ranges may be determined in vitro using the methods described herein.

The compounds of the invention may be characterized as producing an inhibitory effect on tumor cell or endothelial cell proliferation, migration, invasion, or on angiogenesis, on tumor metastasis or on inflammatory reactions. The compounds are especially useful in producing an anti-tumor effect in a mammalian host, preferably human, harboring a tumor wherein angiogenesis inhibition results in reduction in size or growth rate of the tumor or destruction of the tumor. Preferably, the subject is a human.

A longer example of a disease or condition against which the above method is effective include primary growth of a solid tumor, leukemia or lymphoma; tumor invasion, metastasis or growth of tumor metastases; benign hyperplasia; atherosclerosis; myocardial angiogenesis; post-balloon angioplasty vascular restenosis; neointima formation following vascular trauma; vascular graft restenosis; coronary collateral formation; deep venous thrombosis; ischemic limb angiogenesis; telangiectasia; pyogenic granuloma; corneal disease; rubeosis; neovascular glaucoma; diabetic and other retinopathy; retrolental fibroplasia; diabetic neovascularization; macular degeneration; endometriosis; arthritis; fibrosis associated with a chronic inflammatory condition, traumatic spinal cord injury including ischemia, scarring or fibrosis; lung fibrosis, chemotherapy-induced fibrosis; wound healing with scarring and fibrosis; peptic ulcers; a bone fracture; keloids; or a disorder of vasculogenesis, hematopoiesis, ovulation, menstruation, pregnancy or placentation associated with pathogenic cell invasion or with angiogenesis.

A preferred disease or condition to be treated by the above method is tumor growth, invasion or metastasis. This in includes brain tumors. Examples of such brain tumors are astrocytoma, anaplastic astrocytoma, glioblastoma, glioblastoma multiformae, pilocytic astrocytoma, pleiomorphic xanthoastrocytoma, subependymal giant cell astrocytoma, fibrillary astrocytoma, gemistocytic astrocytoma, protoplasmic astrocytoma, oligodendroglioma, anaplastic oligodendroglioma, ependymoma, anaplastic ependymoma, myxopapillary ependymoma, subependymoma, mixed oligoastrocytoma and malignant oligoastrocytoma.

The method is also used to treat a uterine disease such as endometriosis and pathogenic ocular neovascularization such as that associated with, or a cause of, proliferative diabetic retinopathy, neovascular age-related macular degeneration, retinopathy of prematurity, sickle cell retinopathy or retinal vein occlusion.

Angiogenesis inhibitors may play a role in preventing inflammatory angiogenesis and gliosis following traumatic spinal cord injury, thereby promoting the reestablishment of neuronal connectivity (Wamil, A W et al., *Proc. Nat'l. Acad. Sci. USA* 95:13188-13193 (1998)). Therefore, the compositions of the present invention are administered as soon as possible after traumatic spinal cord injury and for several days up to about two weeks thereafter to inhibit the angiogenesis and gliosis that would sterically prevent reestablishment of neuronal connectivity. The treatment reduces the area of damage at the site of spinal cord injury and facilitates regeneration of neuronal function and thereby prevents paralysis. The compounds of the invention are expected also to protect axons from Wallerian degeneration, reverse aminobutyrate-mediated depolarization (occurring in traumatized neurons), and improve recovery of neuronal conductivity of isolated central nervous system cells and tissue in culture.

General Recombinant DNA Methods

General methods of molecular biology have been amply described in the art (Sambrook, et al., *Molecular Cloning: A Laboratory Manual*, 2nd (or later) Edition, Cold Spring Harbor Press, Cold Spring Harbor, N.Y., 1989; Ausubel, F et al., *Current Protocols in Molecular Biology*, Vol. 2, Wiley-Interscience, New York, (current edition); Kriegler, *Gene Transfer and Expression: A Laboratory Manual* (1990); Glover, D M, ed., *DNA Cloning: A Practical Approach*, vol. I & II, IRL Press, 1985; Alberts, B. et al., *Molecular Biology of the Cell*, 4th (or later) Ed., Garland Publishing, Inc., New York, N.Y. (2002); Watson, J D et al., *Recombinant DNA*, 2nd Ed. (or later) Ed., WH Freeman & Co.; 2nd edition (1993); and Old, R W et al., *Principles of Gene Manipulation: An Introduction to Genetic Engineering*, 5th (or later) ed., Univ. of Calif. Press, Berkeley (1994).

Unless otherwise indicated, a particular nucleic acid sequence is intended to encompasses conservative substitution variants thereof (e.g., degenerate codon substitutions) and a complementary sequence. The term "nucleic acid" is synonymous with "polynucleotide" and is intended to include a gene, a cDNA molecule, an mRNA molecule, as well as a fragment of any of these such as an oligonucleotide, and further, equivalents thereof (explained more fully below). Sizes of nucleic acids are stated either as kilobases (kb) or base pairs (bp). These are estimates derived from agarose or polyacrylamide gel electrophoresis (PAGE), from nucleic acid sequences which are determined by the user or published. Protein size is stated as molecular mass in kilodaltons (kDa) or as length (number of amino acid residues). Protein size is estimated from PAGE, from sequencing, from presumptive amino acid sequences based on the coding nucleic acid sequence or from published amino acid sequences.

Specifically, DNA molecules encoding the amino acid sequence corresponding to the polypeptides of the present invention, or active variants thereof, can be synthesized by the polymerase chain reaction (PCR) (see, for example, U.S. Pat. No. 4,683,202) using primers derived the sequence of the protein disclosed herein. These cDNA sequences can then be assembled into a eukaryotic or prokaryotic expression vector and the resulting vector can be used to direct the synthesis of the fusion polypeptide or its fragment or derivative by appropriate host cells, for example COS or CHO cells.

The term "nucleic acid" as used herein is intended to include such fragments or equivalents. The nucleic acid sequences of this invention can be DNA or RNA.

Prokaryotic or eukaryotic host cells transformed or transfected to express the present polypeptides are within the scope of the invention. For example, the polypeptide may be expressed in bacterial cells such as *E. coli*, insect cells (baculovirus), yeast, or mammalian cells such as Chinese hamster ovary cells (CHO) or human cells (which are preferred for human therapeutic use of the transfected cells). Other suitable host are known to those skilled in the art. Expression in eukaryotic cells leads to partial or complete glycosylation and/or formation of relevant inter- or intra-chain disulfide bonds of the recombinant polypeptide. Examples of vectors for expression in yeast *S. cerevisiae* include pYepSec1 (Baldari et al., 1987, *EMBO J.* 6:229-234), pMFa (Kurjan et al. 1982 *Cell* 30:933-943), pJRY88 (Schultz et al., 1987, *Gene* 54:113-123), and pYES2 (Invitrogen Corporation, San Diego, Calif.). Baculovirus vectors available for expression of proteins in cultured insect cells (SF 9 cells) include the pAc series (Smith et al., 1983, *Mol. Cell. Biol.* 3:2156-2165) and the pVL series (Lucklow et al., (1989) *Virology* 170:31-39). Generally, COS cells (Gluzman 1981 *Cell* 23:175-182) are used in conjunction with such vectors as pCDM 8 (Aruffo et al., supra, for transient amplification/expression in mammalian cells, while CHO (dhfr-negative CHO) cells are used with vectors such as pMT2PC (Kaufman et al., 1987, *EMBO J.* 6:187-195) for stable amplification/expression in mammalian cells. The NS0 myeloma cell line (a glutamine synthetase expression system) is available from Celltech Ltd.

Construction of suitable vectors containing the desired coding and control sequences employs standard ligation and restriction techniques which are well understood in the art. Isolated plasmids, DNA sequences, or synthesized oligonucleotides are cleaved, tailored, and re-ligated in the form desired. The DNA sequences which form the vectors are available from a number of sources. Backbone vectors and control systems are generally found on available "host" vectors which are used for the bulk of the sequences in construction. For the pertinent coding sequence, initial construction may be, and usually is, a matter of retrieving the appropriate sequences from cDNA or genomic DNA libraries. However, once the sequence is disclosed it is possible to synthesize the entire gene sequence in vitro starting from the individual nucleotide derivatives. The entire gene sequence for genes of length in the range of 500-1000 bp may be prepared by synthesizing individual overlapping complementary oligonucleotides and filling in single stranded nonoverlapping portions using DNA polymerase in the presence of the deoxyribonucleotide triphosphates. This approach has been used successfully in the construction of several genes of known sequence. See, for example, Edge, *Nature* 1981, 292:756; Nambair et al., *Science* 1984, 223:1299; and Jay, *J. Biol. Chem.* 1984, 259:6311. Synthetic oligonucleotides are prepared by methods described in references cited above or by Beaucage et al., *Tetrahedron Lett.* 1981, 22:1859; and Matteucci et al., *J. Am. Chem. Soc.* 1981, 103:3185.

The components of the desired vectors can be excised and ligated using standard restriction and ligation procedures. Site-specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. If desired, size separation of the cleaved fragments may be performed by standard polyacrylamide gel or agarose gel electrophoresis techniques (e.g., *Meth. Enzymol.* (1980) 65:499-560).

Any of a number of methods are used to introduce mutations into the coding sequence to generate variants if these are to be produced recombinantly. These mutations include simple deletions or insertions, systematic deletions, insertions or substitutions of clusters of bases or substitutions of single bases. Modification of the DNA sequence by site-directed mutagenesis is a well-known technique for which protocols and reagents are commercially available (Zoller et al., *Nucleic Acids Res.* 1982, 10:6487-6500; Adelman et al., *DNA* 1983, 2:183-193)). The isolated DNA is analyzed by restriction and/or sequenced by the dideoxy nucleotide method (Sanger, *Proc. Natl. Acad. Sci. USA* 1977, 74:5463; Messing, et al., *Nucleic Acids Res.* 1981, 9:3091 or Maxam et al., *Meth. Enzymol.*, supra).

Vector DNA can be introduced into mammalian cells via conventional techniques such as calcium phosphate or calcium chloride co-precipitation, DEAE-dextran-mediated transfection, lipofection, or electroporation. Suitable methods for transforming host cells can be found in Sambrook et al. supra and other standard texts. In fusion expression vectors, a proteolytic cleavage site is introduced at the junction of the reporter group and the target protein to enable separation of the target protein from the reporter group subsequent to purification of the fusion protein. Proteolytic enzymes for such cleavage and their recognition sequences include Factor Xa, thrombin and enterokinase.

Having now generally described the invention, the same will be more readily understood through reference to the following examples which are provided by way of illustration, and are not intended to be limiting of the present invention, unless specified.

EXAMPLE I

Materials and Methods

Cell Lines Expressing Proteins

Figure 1:
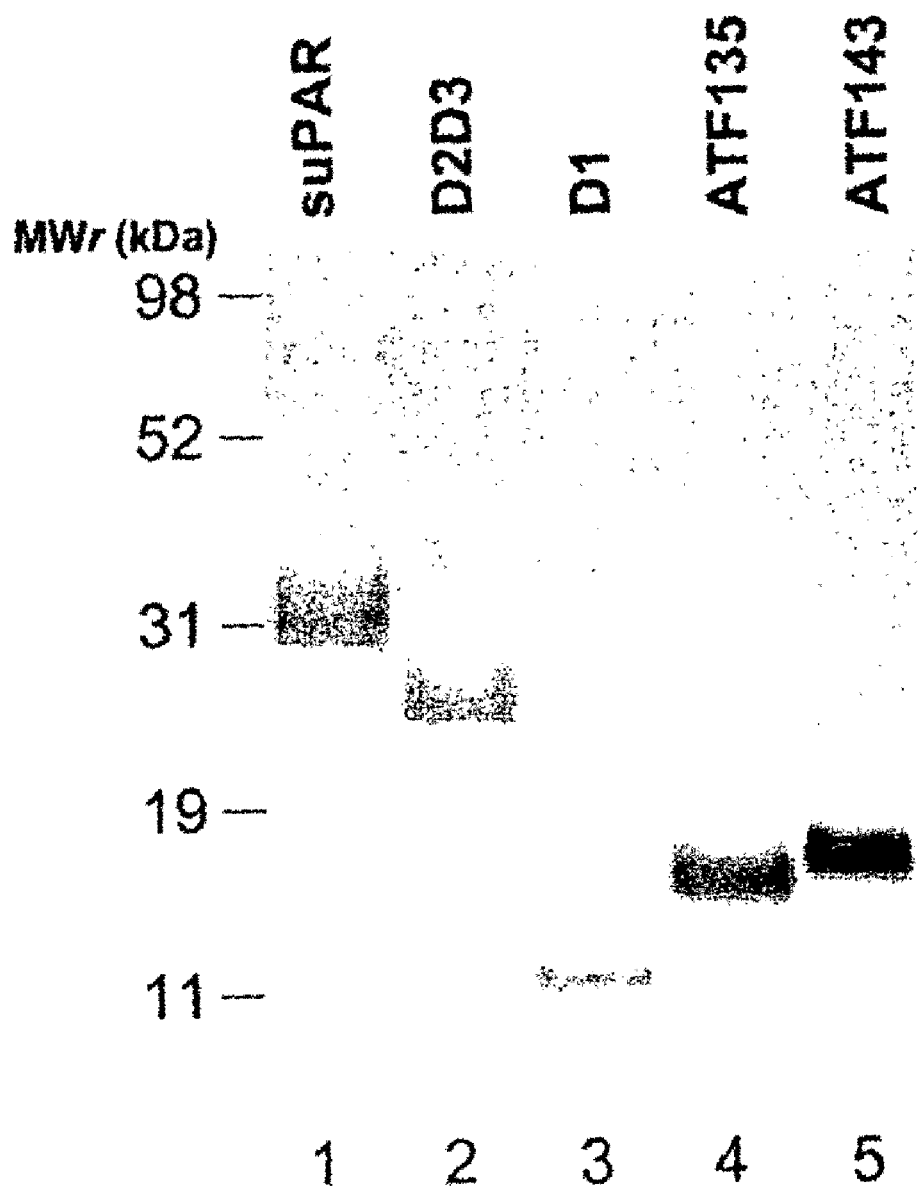
FIG. 1. SDS-PAGE analysis of ATF and suPAR fragments expressed in S2 cells. ATF (aa 1-143) and suPAR (aa 1-279) were cloned and expressed in *Drosophila* Schneider S2 cells. Cells were induced to express recombinant proteins with copper (0.5 nM) for 7 days. Culture supernatants were collected and clarified by centrifugation and filtration. After addition of protease inhibitors proteins were purified by ion exchange chromatography on either DEAE-Sepharose, pH 7.5, (ATF) or SP-Sepharose, pH 8.8, (suPAR). ATF and suPAR were further purified using RP-HPLC. Purified, recombinant suPAR was digested with chymotrypsin to generate the soluble domain2/domain3 (D2D3) fragment. Prior to immunization, D2D3 protein was conjugated to the carrier protein keyhole limpet hemocyanin (KLH).

The *Drosophila* expression system (DES™; Invitrogen, Inc.) utilizes the Schneider 2 (S2) cell line, derived from *Drosophila melanogaster*, and plasmid vectors for the expression of heterologous proteins. The plasmid vectors for expression in S2 cells are very versatile, allowing inducible expression of a protein driven by the metallothionein (MT) promoter. The same plasmid also allows the protein to be secreted from the cell into the surrounding media, greatly simplifying protein purification. Multiple copies of the vector can be stably inserted into the genomic DNA of S2 cells, increasing levels of protein expression. Proteins expressed in S2 cells are minimally glycosylated, which is important for the generation of Abs directed against the protein component of uPAR. Typical yields of protein following purification are 25-50 mg/L with a purity of approximately 95 percent (FIG. 1). Cell lines expressing the following proteins have been generated: suPAR, D1, D2D3, scuPA, ATF1-143, ATF1-135, Kringle47-143, and Kringle47-135. In addition, clones have been generated for suPAR in which the N-linked glycosylation sites have been abolished.

Reagents $^{125}$I was purchased as Na$^{125}$I (480-630 MBq [13-17 mCi] per µg iodine) from the Amersham Corp.

Tumor Cell Lines

The following cell and tumor lines were used: A549, HeLa, and A2780. The A2780 human ovarian cancer line was established from tumor tissue from an untreated patient. A2780 cells are maintained as a monolayer in RPMI 1640 medium supplemented with 2 mM glutamine, 0.01 mg/mL bovine insulin, and 10% FBS (supra). A549, human lung carcinoma, ATCC Catalog No. CCL-185, described above, are maintained in Ham's F12K medium supplemented with 2 mM L-glutamine, 0.15% NaHCO3, and 10% FBS.

A2780 cells ($2 \times 10^6$) were inoculated in the right flank of nude Balb/c female mice. The tumor was staged to 50 to 200 mm$^3$ range before treatment was initiated. The IgG control Ab as well as the anti-D2D3 uPAR mAbs were administered intraperitoneally at 10 mg/kg twice weekly on Monday and Friday. The cisplatin treatment group was staged to 1000 mm$^3$; animals received 6 mg/kg once a week. Tumor volumes were measured twice a week.

A549 carcinoma cells ($10^6$) were inoculated in the right flank of C.B-17/Sys (scid/scid) female mice (scid: Severe Combined Immunodeficient). Treatment was started the day after tumor inoculation. The IgG control Ab (and the PBS control) as well as the anti-D2D3 uPAR mAb ATN-658 were administered intraperitoneally 10 mg/kg twice weekly on Monday and Friday. Initially tumor volumes were measured once a week. When the volume in any treatment group exceeded 300 mm$^3$, measurements were obtained twice a week.

At the time of sacrifice, plasma is obtained and the tumor excised from each animal. Half of the tumor is snap frozen for biochemical assessment and the rest is placed in Zinc fixative for histological assessment.

EXAMPLE II

Anti-D2D3 mAbs

Immunization of Balb/c mice with the D2D3 domain of recombinant suPAR conjugated to KLH generated a robust immune response. Subsequent fusion experiments generated parental clones with specific cross-reactivity with the D2D3 domain of uPAR as determined by western blotting and ELISA assays using recombinant proteins. These parental clones were subjected to limiting dilution and a panel of mAbs specific for D2D3 was obtained. The properties of four of these Abs are summarized in Table 3. Isotyping identified all clones as IgG1, κ. Specificity for uPAR was confirmed by western blotting. The affinity of the Abs was determined using direct binding assays. The majority of clones have affinities of 1 to 5 nM.

TABLE 3

Anti-D2D3 (uPAR) antibodies

| Clone # | Isotype | Western Blot (suPAR) | $K_D$ (nM) |
|---|---|---|---|
| ATN-615 | IgG1, κ | + | 2 |
| ATN-658 | IgG1, κ | + | 1 |
| ATN-616 | IgG1, κ | + | 5 |
| ATN-617 | IgG1, κ | + | 3 |

Figure 3:
FIG. 3. Western blots with two anti-D2D3 mabs, ATN-615 and ATN-658. Recombinant proteins were resolved by SDS-PAGE and transferred to PVDF membranes. Membranes were probed with purified antibodies (5 μg/ml). ATN-615 and ATN-658 specifically recognize suPAR and D2D3.

The results of Western blotting experiments using two of these Abs, ATN-615 and ATN-658, are shown in FIG. 3. Both of the mAbs specifically recognize suPAR and, specifically, the D2D3 domain of uPAR.

Figure 4:
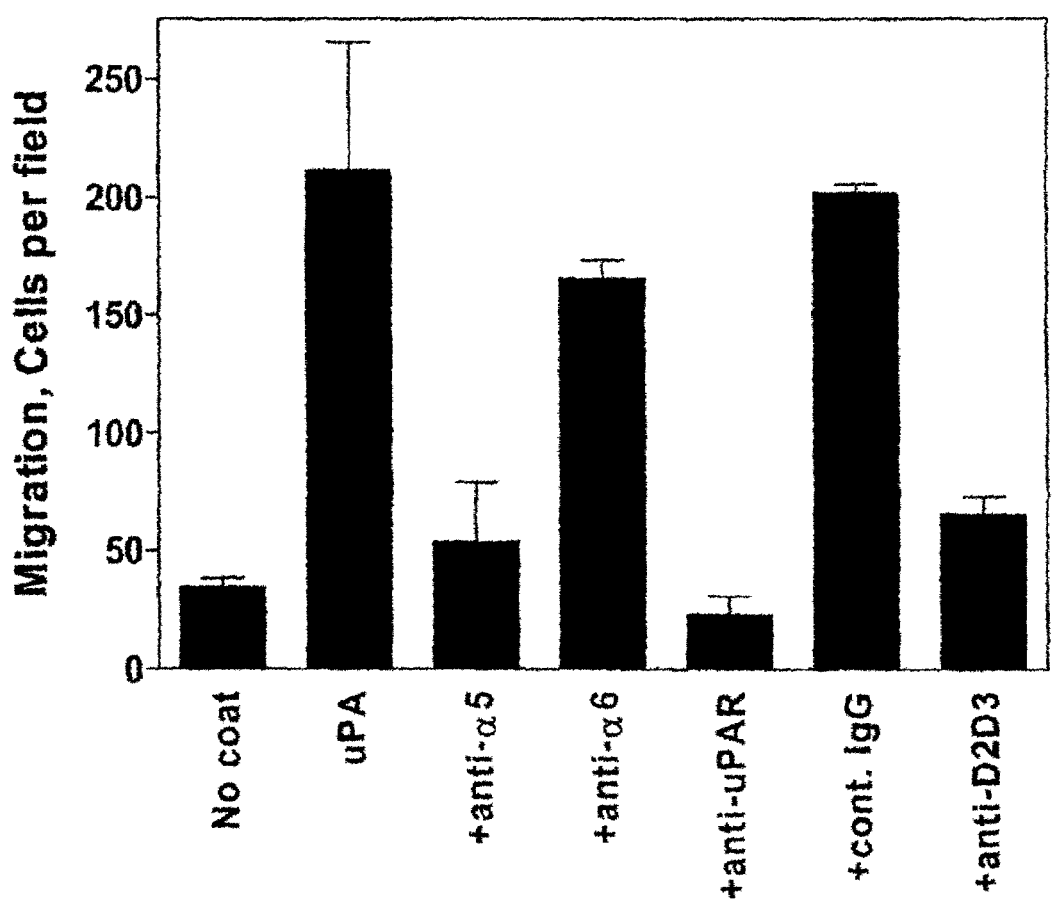
FIG. 4. Anti-D2D3 antibodies inhibit uPA-induced migration. Migration of uPAR expressing CHO cells toward uPA (500 nM) was determined using a modified Boyden chamber assay. Anti-integrin α5, anti-uPAR, and anti-D2D3 antibodies inhibit migration, suggesting that integrin α5β1 and uPAR are critical for uPA-induced migration.

The functional activity of the anti-D2D3 antibodies was tested in migration assays. Previous experiments have demonstrated that uPAR-expressing CHO cells migrate towards uPA in a modified Boyden chamber assay (FIG. 4) and that this migration is dependent of the GFD of uPA (not shown). As shown in FIG. 4, cell migration is inhibited by a mAb specific for D2D3 as well as a rabbit polyclonal Ab directed against uPAR. Interestingly, cell migration is also inhibited by anti-α5 integrin Abs but not by anti-α6 integrin Abs. Taken together, these data suggest that integrin α5β1 and uPAR are critical for uPA-induced migration.

Figure 5:
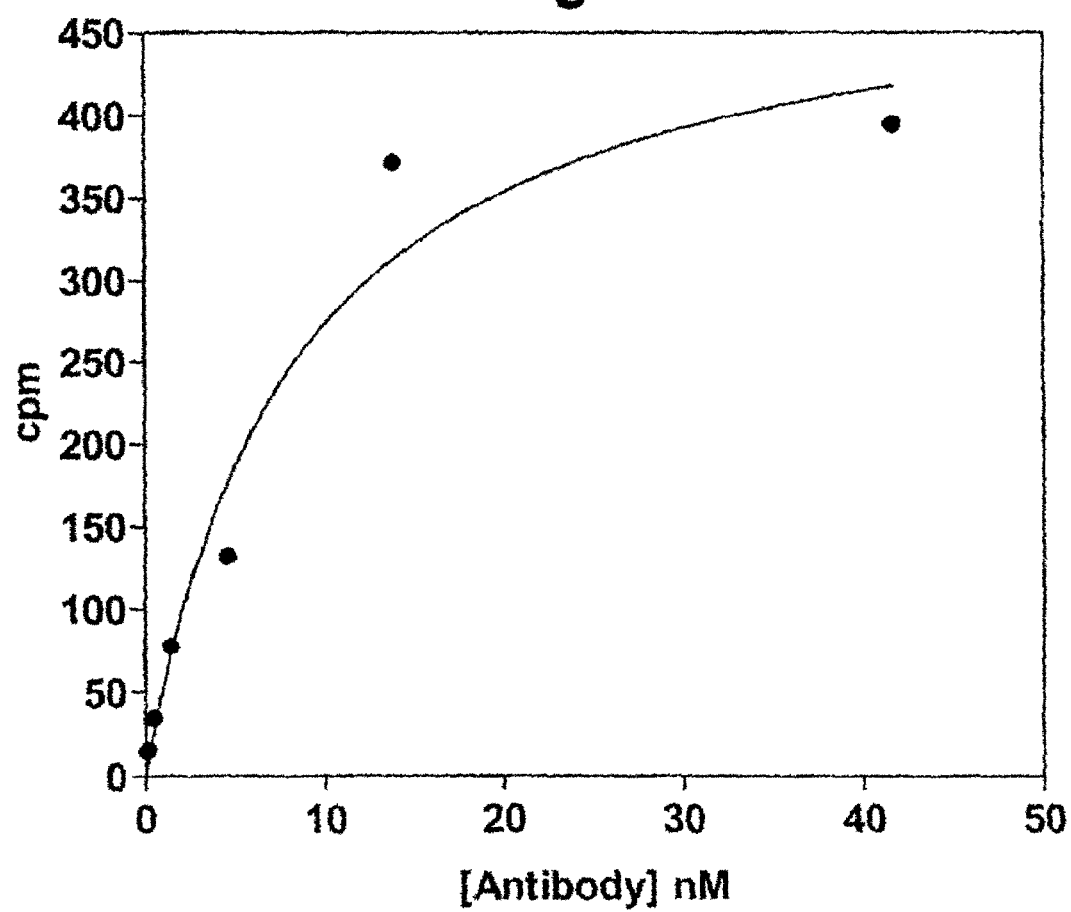
FIG. 5. $^{125}$I-labeled ATN-658 binds to HeLa cells with high affinity. Confluent monolayers of HeLa cells in 24-well plates were incubated with increasing concentrations of [$^{125}$I]-ATN-658 at room temperature for one hour. Cells were washed extensively with PBS/Tween-20 and bound material was solubilized with 1 M NaOH. Non-specific binding was determined in the presence of a 100-fold excess of unlabeled Ab.
Figure 6:
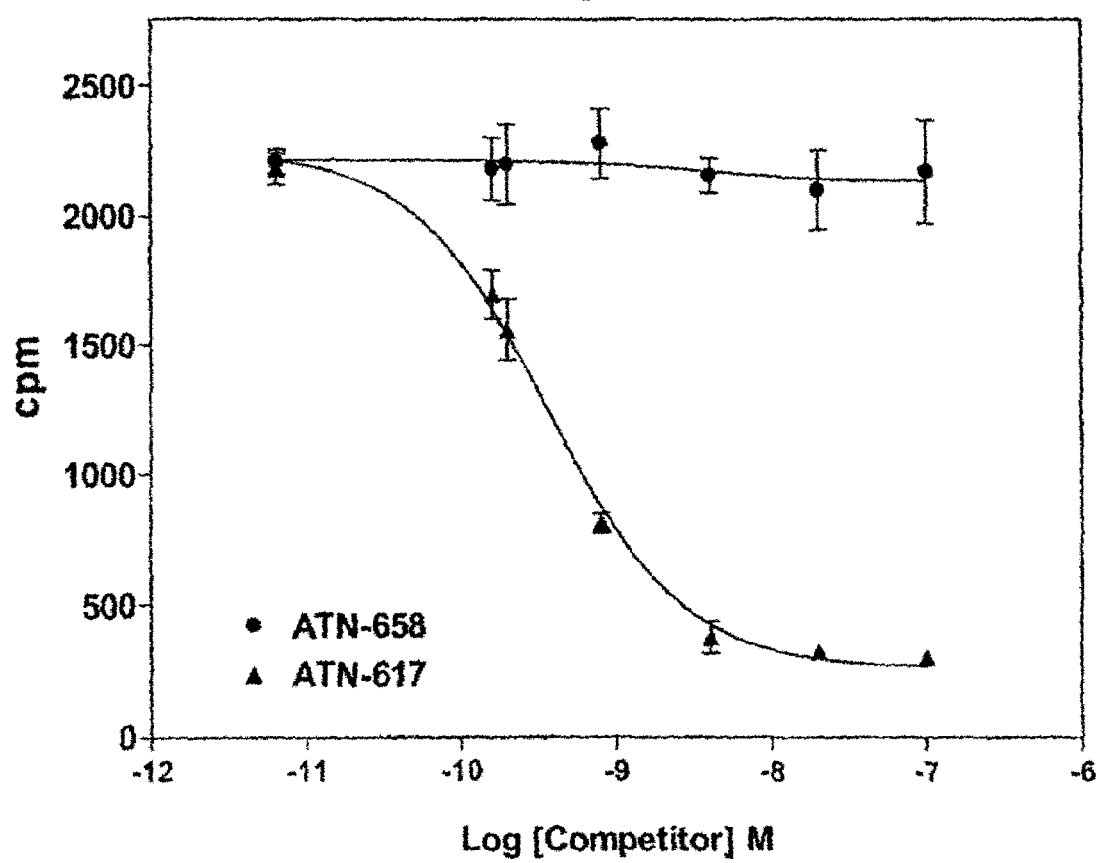
FIG. 6. shows that the mAb ATN-658 does not compete with binding of uPA to HeLa cells. Binding of ATN-658 to HeLa cells did not inhibit binding of $^{125}$I-scuPA. HeLa cells were incubated with 5 nM $^{125}$I-scuPA in the presence or absence of either 300 nM unlabeled scuPA or 300 nM ATN-658. ATN-617, an anti-uPAR mAb that blocks the binding of uPA to uPAR is shown to compete with scuPA binding.

The utility of the various anti-D2D3 Abs for diagnostic imaging or targeting of therapeutic agents is dependent on their ability to bind uPAR on the cell surface with high affinity. As shown in FIG. 5, iodinated Ab ATN-658 binds to HeLa cells with a $K_D$ of approx. 1.5 nM. This is consistent with the $K_D$ for this Ab determined in direct binding experiments (Table 3), indicating that binding is unaffected by the labeling process.

uPA may be bound to the uPAR receptor on the surface of tumor or endothelial cells in vivo. Thus, Abs that bind to uPAR in the presence of uPA therefore have additional utility as diagnostic or targeting agents. mAb ATN-658 does not inhibit the binding of scuPA to uPAR (FIG. 6) on the surface of HeLa cells and is able to bind to HeLa cells in the presence of scuPA. Thus, ATN-658 can target both occupied and unoccupied receptors on the cell surface.

The amino acid sequences of consensus $V_L$ and $V_H$ chains, including the three CDR regions of ANT-658 and ATN-615 were determined by standard methods and have been set forth above, and therefore are not repeated here, although they should be considered as incorporated into this exemplary disclosure.

EXAMPLE III

Binding of uPA to uPAR

Binding of uPA to uPAR was measured using $^{125}$I-labeled uPA and HeLa cells. HeLa cells express abundant amounts of uPAR but do not express uPA. Briefly, 100 μg of scuPA was labeled with 100 μCi of [$^{125}$I]NaI using IodoGen™ iodination reagent (Pierce Biotechnology Inc.). Unincorporated labeled NaI was removed from the labeled protein using a size exclusion column and the labeled protein eluted in Tris-buffered saline containing 0.1% bovine serum albumin (BSA). HeLa cells were incubated with increasing concentrations of [$^{125}$I]-scuPA diluted in PBS containing 0.1% BSA for 2 h at 4° C. Cells were washed extensively with PBS/0.1% BSA, the cell monolayers lysed with 1M NaOH and the total number of bound counts determined. Specific binding was determined by incubating cells with [$^{125}$I]-scuPA in the presence of a large excess of unlabeled scuPA. Binding was also performed with MDA-MB231 cells which express both uPA and uPAR. To determine binding of scuPA, endogenous uPA is first removed from the surface of MDA-MB231 cells by washing with a buffer containing 0.1 M glycine/100 mM NaCl, pH 3 for 5 minutes at 4° C. This protocol was also used to determine binding of [$^{125}$I]-ATF to HeLa cells. The ability of Abs to inhibit the binding of either [$^{125}$I]-scuPA or [$^{125}$I]-ATF binding to HeLa cells was determined by incubating cells with increasing amounts of the unlabeled Ab for 15 minutes at 4° C., prior to the addition of the [$^{125}$I]-labeled protein.

EXAMPLE IV

Inhibition of Cell Migration

Inhibition of cell migration by Abs specific for uPA or uPAR was tested using a modified Boyden chamber assay as described previously (Tarui, T et al., (2003) J. Biol. Chem., 278:29863-29872). Briefly, the lower side of a Boyden chamber filter was coated with 500 nM uPA and serum free migration buffer (Dulbecco's modified Eagle's medium containing 10 mM Hepes and 0.5% bovine serum albumin) added to the lower chamber. uPAR-expressing CHO cells were resuspended in serum free migration buffer ($8 \times 10^5$ cells/ml) and 100 μl added to the upper chamber. To test the ability of anti-uPA or anti-uPAR Abs to inhibit cell migration, cells were pre-incubated with 10 μg/ml Ab for 15 minutes prior to addition to the upper chamber. The cells were then incubated at 37° C. in 5% $CO_2$ for 20 h. Cells migrating to the lower chamber were detected by staining with 0.5% crystal violet and light microscopy.

EXAMPLE V

Assay for Antibodies that Recognize the Same Epitope as ATN-658 Using Biotinylated ATN-658

Figure 9:
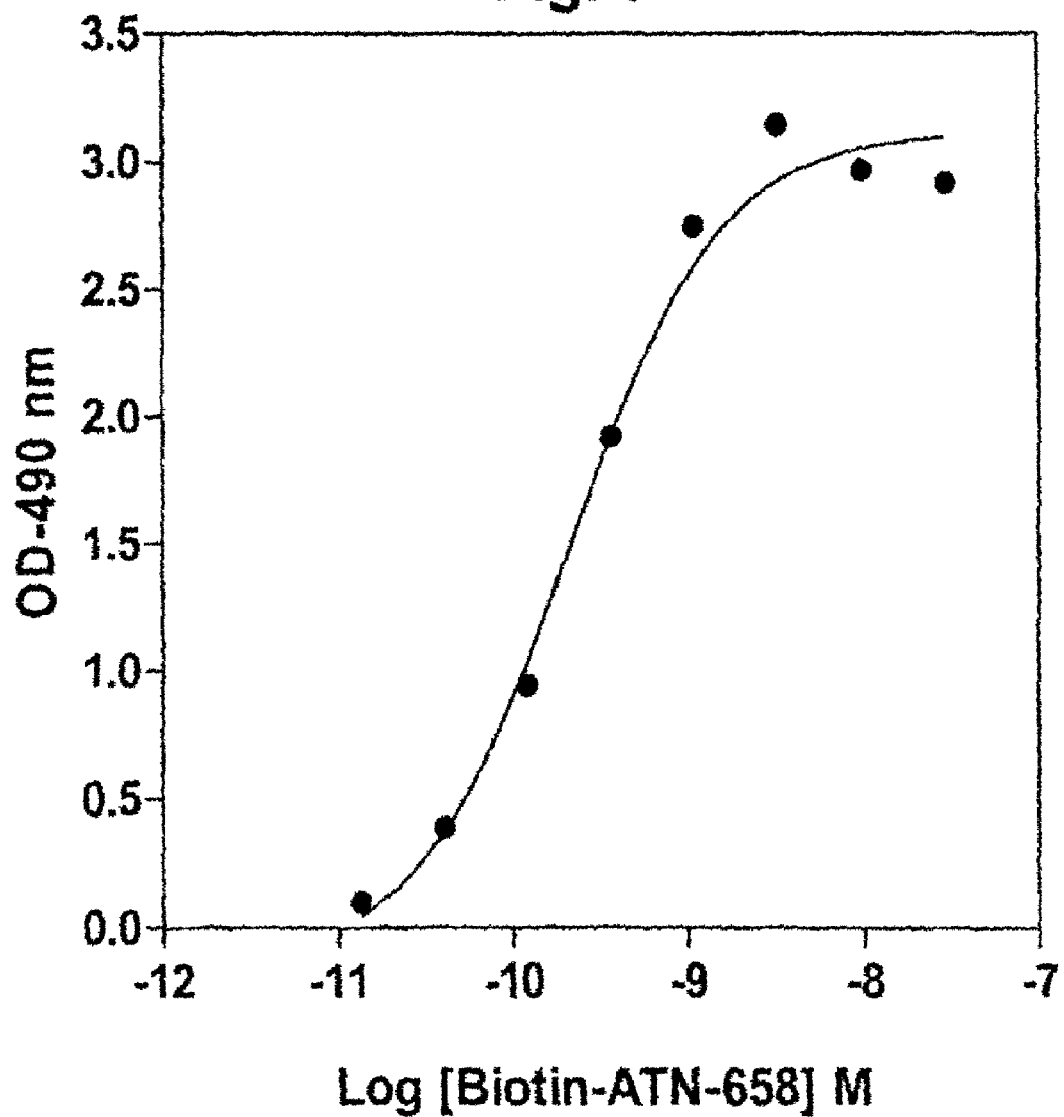
FIG. 9 shows that biotinylated ATN-658 binds saturably to suPAR.

The anti-D2D3 Ab, ATN-658, was biotinylated using EZ-link™ sulfo-NHS-LC-biotin (Pierce Biotechnology Inc.) according to the manufactures instructions. Typically, a 20-fold molar excess of the biotin-labeling reagent was used to label ATN-658 and unincorporated biotin removed from the labeled Ab using a size exclusion column. To ensure that the labeled Ab retained its affinity for uPAR, Biotin-ATN-658 was tested in an ELISA assay for binding to suPAR. Bound Biotin-ATN-658 was detected using HRP-conjugated streptavidin. Biotin labeling did not reduce the affinity of ATN-658 for suPAR (FIG. 9). To identify Abs that recognize the same epitope as ATN-658 a competition assay was established. Briefly, 96-well EIA/RIA high protein binding plates were coated with 100 ng/well of suPAR overnight at 4° C. After the blocking of non-specific binding with 1% casein, plates were washed with PBS and Abs to be tested, diluted in PBS/0.1% casein containing 0.2 nM Biotin-ATN-658, added to the appropriate wells. Plates were incubated for a further 1 h at room-temperature, washed extensively with PBS/0.05% Tween-20 and the bound Biotin-ATN-658 detected using HRP-conjugated streptavidin and the appropriate substrate (FIG. 10A/10B).

EXAMPLE VI

Activities of mAbs In Vivo

Antibodies were tested for their ability to inhibit tumor growth in vivo in two models: the A549 non-small cell human lung cancer model and the A2780 ovarian cancer model using the protocols and conditions described in Example I. Treatment was started the day after tumor inoculation. The IgG control Ab (and the PBS control) as well as the anti-D2D3 UPAR mAb ATN-658 was administered by the intraperitoneal route at 10 mg/kg twice weekly on Monday and Friday.

Figure 7:
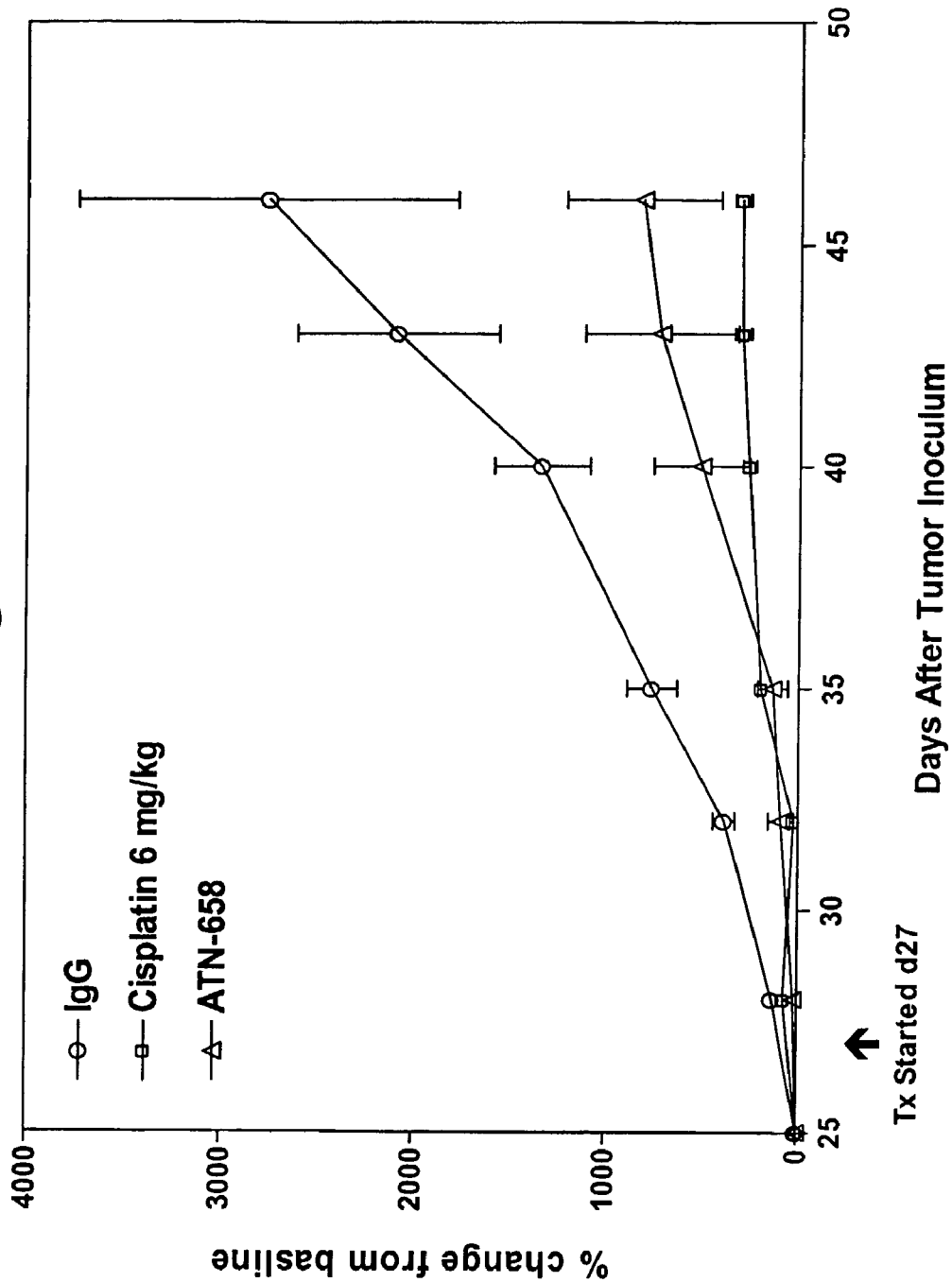
FIG. 7 shows that ATN-658 inhibits tumor growth in the A2780 ovarian cancer model as effectively as cisplatin. A2780 cells express only uPAR and not uPA.
Figure 8:
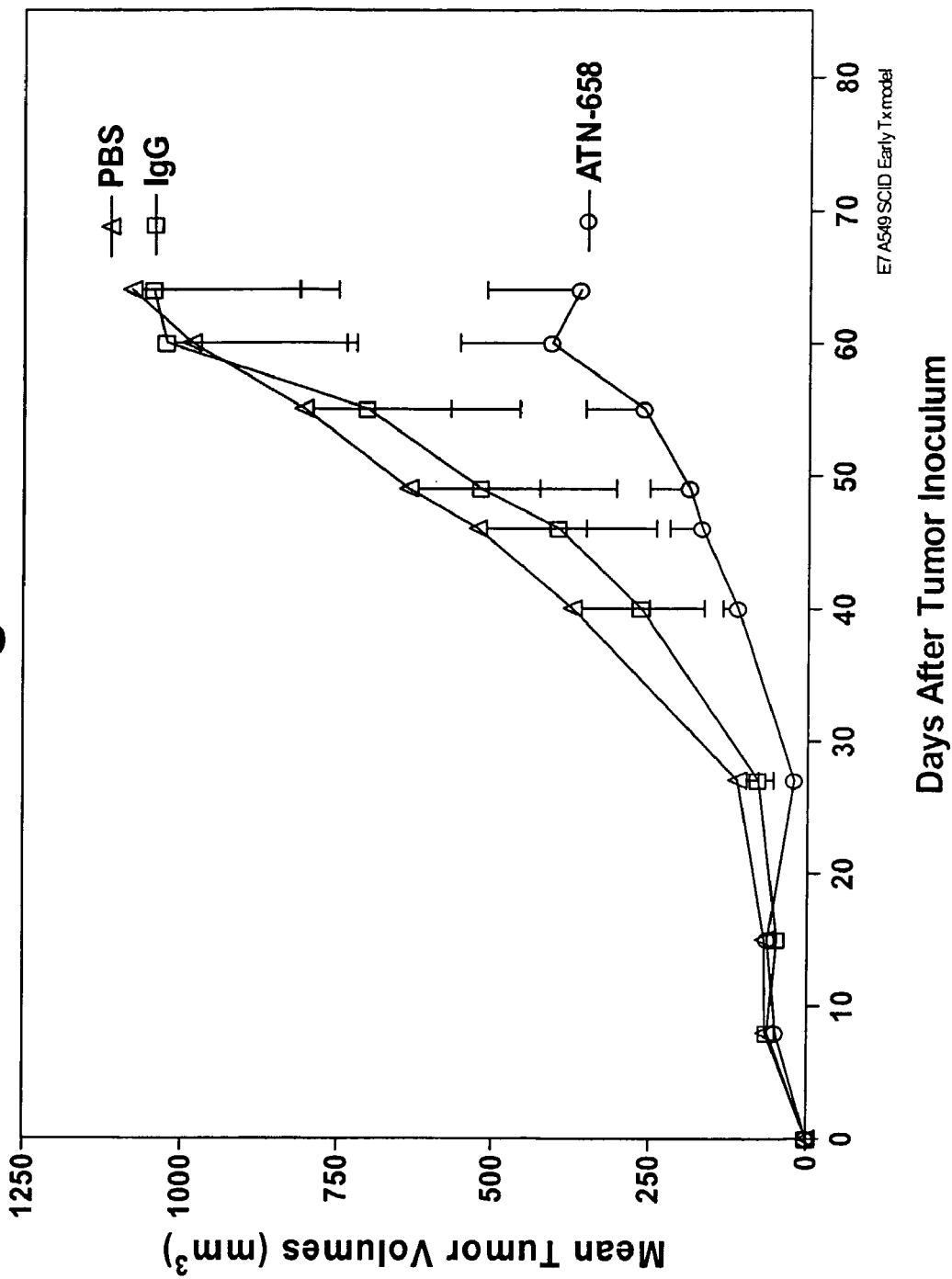
FIG. 8 shows that ATN-658 inhibits tumor growth in an A549 lung cancer (non-small cell) model in which $10^6$ tumor cells were inoculated. A549 cells express both uPA and uPAR.

ATN-658 significantly inhibited growth in both of these models (FIGS. 7 and 8).

All the references cited above are incorporated herein by reference in their entirety, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

In the event of any disagreement between the amino acid sequences disclosed above and those those in the electronic or paper Sequence Listing attached hereto or filed later, the sequences above shall take precedence.

What is claimed is:

1. An antibody ligand or an antigen-binding fragment thereof that binds to a binary uPA-uPAR complex and to a ternary complex of uPA-uPAR with an additional molecule X, which ligand is further characterized by the following properties:
   (a) does not substantially bind to (i) free uPA or (ii) the region of uPAR that recognizes and binds to uPA, so that the ligand does not inhibit uPA-uPAR binding
   (b) does not substantially bind to any of the following:
      (i) a uPA-X complex,
      (ii) the uPA-recognizing and uPA-binding region of X,
      (iii) free uPA, and
      (iv) free X; and
   (c) does not substantially inhibit uPA binding with uPAR or with X, and
wherein the antibody or fragment comprises the structural properties of (1) or (2), below
   (1) the antibody or antigen-binding fragment comprises:
      (A) a $V_L$ chain comprising three CDR's which have the respective combination of amino acids sequences
         (1) SEQ ID NO:3, SEQ ID NO:4 and SEQ ID NO:5; or
         (2) SEQ ID NO:11, SEQ ID NO:12 and SEQ ID NO:13; and
      /(B) a $V_H$ chain comprising three CDR's which have the respective combination of amino acids sequences
         (1) SEQ ID NO:6, SEQ ID NO:7 and SEQ ID NO:8, or
         (2) SEQ ID NO:14, SEQ ID NO:15 and SEQ ID NO:16, or
   (2) the antibody or antigen-binding fragment comprises:
      (A) a $V_L$ chain that has the sequence SEQ ID NO:1 or SEQ ID NO:9; and
      (B) a $V_H$ chain that has the sequence SEQ ID NO:2 or SEQ ID NO:10.

2. The antibody ligand of claim 1 wherein said antibody is a monoclonal antibody (mAb).

3. The mAb of claim 2 that is selected from the group consisting of:
   (a) a mAb designated ATN-615 produced by hybridoma having ATCC Accession #PTA-8192); and
   (b) a mAb designated ATN-658 produced by hybridoma having ATCC Accession #PTA-8191.

4. The antibody ligand of claim 1 that, when bound to the uPA-uPAR complexes, inhibits binding of the complexes with another biological ligand for these complexes.

5. The antibody ligand of claim 1, wherein the binding to the complexes interferes with and inhibits
   (a) uPAR mediated assembly of fibronectin (Fn),
   (b) binding of Fn or a Fn fragment to an integrin, or
   (c) the assembly of vitronectin components.

6. The antibody ligand of claim 1 that is:
   (a) diagnostically detectably labeled, or
   (b) labeled with, conjugated to, or fused to, a therapeutically active moiety, rendering said antibody ligand therapeutically active.

7. The mAb of claim 3 that is:
   (a) diagnostically detectably labeled or
   (b) labeled with, conjugated to, or fused to, a therapeutically active moiety, rendering said ligand therapeutically active.

8. The mAb of claim 2 that is
   (a) diagnostically detectably labeled or
   (b) labeled with, conjugated to, or fused to, a therapeutically active moiety, rendering said ligand therapeutically active.

9. A diagnostic composition comprising:
   (a) the diagnostically-labeled antibody ligand of claim 6; and
   (b) a diagnostically acceptable carrier.

10. The composition of claim 9 wherein the antibody ligand is labeled with
   (a) one of the following radionuclides: $^{3}$H, $^{14}$C, $^{35}$S, $^{67}$Ga, $^{68}$Ga, $^{72}$As, $^{89}$Zr, $^{97}$Ru, $^{99}$Tc, $^{111}$In, $^{123}$I, $^{125}$I, $^{131}$I, $^{169}$Yb or $^{201}$Tl,
   (b) a PET-imageable agent,
   (c) an MRI-imageable agent,
   (d) a fluorescer or fluorogen,
   (f) a chromophore or chromogen,
   (g) a phosphorescer,
   (h) a chemiluminescer, or
   (i) a bioluminescer.

11. A pharmaceutical composition comprising:
   (a) an effective amount of the therapeutically active monoclonal antibody of claim 7; and
   (b) a pharmaceutically acceptable carrier.

12. A pharmaceutical composition comprising:
   (a) an effective amount of the therapeutically active monoclonal antibody of claim 8; and
   (b) a pharmaceutically acceptable carrier.

13. The therapeutic pharmaceutical composition of claim 11 wherein the therapeutically active moiety is
   (a) a chemotherapeutic drug,
   (b) a toxin or other peptide or polypeptide fused to said ligand, or
   (c) one of the following therapeutic radionuclides: $^{47}$Sc, $^{67}$Cu, $^{90}$Y, $^{109}$Pd, $^{125}$I, $^{131}$I, $^{186}$Re, $^{188}$Re, $^{199}$Au, $^{211}$At, $^{212}$Pb or $^{217}$Bi.

14. A method for inhibiting cell migration, cell invasion, cell proliferation or angiogenesis, or for inducing apoptosis, comprising contacting cells associated with undesired cell migration, invasion, proliferation or angiogenesis with an effective amount of the antibody or antigen binding fragment of claim 1.

15. A method for treating a subject having a disease, disorder or condition characterized by undesired angiogenesis, tumor growth and/or tumor metastasis comprising administering to the subject an effective amount of the mAb or antigen binding fragment of claim 2.

16. An assay method for detecting in a sample a substance suspected of having the binding properties of the ligand of claim 1, comprising
 (a) contacting the sample with uPA-uPAR complexes and determining binding of a component of said sample to the complexes;
 (b) contacting the sample with free uPAR and determining binding of a component of said sample to the uPAR.
 (c) comparing the binding of (a) and (b),
wherein the presence of binding in (a) and a substantial absence or significantly lower binding in (b) is indicative of the present of said substance in the sample.

17. The method of claim 16 wherein the suspected substance is an antibody or antigen binding fragment thereof.

18. An assay method for detecting in a sample a substance suspected of having the binding properties of the ligand of claim 1, comprising
 (a) contacting the sample with uPA-uPAR-X complexes and determining binding of a component of said sample to the complexes;
 (b) contacting the sample with one or more of
  (i) uPA:X complexes
  (ii) uPA-uPAR complexes or
  (iii) uncomplexed X
  and determining binding of a component of said sample to uPA-X, uPA-uPAR or X;
 (c) comparing the binding of (a) and (b),
wherein the presence of binding in (a) and a substantial absence or significantly lower binding in (b) is indicative of the present of said substance in the sample.

19. The mAb of claim 3 that is the mAb designated ATN-658 produced by hybridoma having ATCC Accession #PTA-8191 or the antigen binding fragment of ATN-658.

20. The mAb of claim 8 that is the mAb designated ATN-658 produced by hybridoma having ATCC Accession #PTA-8191.

21. A pharmaceutical composion comprising:
 (a) the mAb of claim 19; and
 (b) a pharmaceutically acceptable carrier.

22. The method according to claim 14 wherein the antibody is the mAb designated ATN-658 produced by hybridoma having ATCC Accession #PTA-8191 and the fragment is an antigen binding fragment of ATN-658.

23. The method according to claim 15 wherein the antibody is the mAb designated ATN-658 produced by hybridoma having ATCC Accession #PTA-8191 and the fragment is an antigen-binding fragment of ATN-658.

24. The method according to claim 15 wherein the disease, disorder or condition is cancer.

25. The method according to claim 23 wherein the disease, disorder or condition is cancer.

26. The method according to claim 24 wherein the cancer is lung cancer, ovarian cancer, prostate cancer, pancreatic cancer or colon cancer.

27. The method according to claim 25 wherein the cancer is lung cancer, ovarian cancer, prostate cancer, pancreatic cancer or colon cancer.

* * * * *